(12) United States Patent
Michaeli et al.

(10) Patent No.: US 11,304,618 B2
(45) Date of Patent: Apr. 19, 2022

(54) METHOD AND APPARATUS FOR NONINVASIVE ABSOLUTE (MEAN) INTRACRANIAL PRESSURE (A-ICP) MEASUREMENT AND/OR MONITORING

(71) Applicants: David Michaeli, Ashkelon (IL); Menashe Michaeli, Vilnius (LT)

(72) Inventors: David Michaeli, Ashkelon (IL); Menashe Michaeli, Vilnius (LT)

( * ) Notice: Subject to any disclaimer, the term of this patent is extended or adjusted under 35 U.S.C. 154(b) by 0 days.

(21) Appl. No.: 17/373,898

(22) Filed: Jul. 13, 2021

(65) Prior Publication Data

US 2021/0338093 A1 Nov. 4, 2021

Related U.S. Application Data

(63) Continuation of application No. 16/928,165, filed on Jul. 14, 2020, now Pat. No. 11,058,313, which is a (Continued)

(51) Int. Cl.
*A61B 5/03* (2006.01)
*A61B 5/00* (2006.01)
(Continued)

(52) U.S. Cl.
CPC ............ *A61B 5/031* (2013.01); *A61B 5/0053* (2013.01); *A61B 5/6814* (2013.01); (Continued)

(58) Field of Classification Search
CPC ..... A61B 5/031; A61B 5/7257; A61B 5/0053; A61B 5/6814; A61B 8/5223; A61B 8/4444
See application file for complete search history.

(56) References Cited

U.S. PATENT DOCUMENTS 5,617,873 A 4/1997 Yost et al.
5,919,144 A 7/1999 Bridger et al.
(Continued)

FOREIGN PATENT DOCUMENTS

WO 2000068647 A2 11/2000
WO 2010151734 A2 12/2010

OTHER PUBLICATIONS

Deb Sanjay Nag, Seelora Sahu, Amlan Swain, Shashi Kant, Intracranial pressure monitoring: Gold standard and recent innovations. Article. Jul. 6, 2019. 20 pages. Baishideng Publishing Group Inc. Pleasanton, United States.
(Continued)

*Primary Examiner* — Jason M Ip
(74) *Attorney, Agent, or Firm* — Mark M. Friedman

(57) ABSTRACT

Non-invasive measurement of intracranial pressure (ICP), for example mean ICP. A probe adjacent the head emits energy, such as ultrasound, and receives reflected signals. A processing unit derives ICP waveform from the signals. A pressure mechanism applies external pressure intermittently to outer surface of the head and incrementally increases the external pressure. The processing unit is configured to detect a decrease in amplitude of the ICP waveform (occurring in some embodiments only after an intermediate period of ICRS compensation), the processing unit configured to determine the ICP of the person from a sum of applied external pressures from a time of the initial value A1 until a final value at which the amplitude remains stable with additional increase in applied external pressure. In some cases, the final value is earlier than that but the processing unit extrapolates the sum to when the amplitude remains stable with additional increases in pressure.

24 Claims, 9 Drawing Sheets

Related U.S. Application Data continuation of application No. 16/695,215, filed on Nov. 26, 2019, now Pat. No. 10,709,345.

(51) Int. Cl.
*A61B 8/00* (2006.01)
*A61B 8/08* (2006.01)

(52) U.S. Cl.
CPC .......... *A61B 5/7257* (2013.01); *A61B 8/4444* (2013.01); *A61B 8/523* (2013.01); *A61B 8/5223* (2013.01)

(56) References Cited

U.S. PATENT DOCUMENTS

| | | |
|---|---|---|
| 6,086,533 A | 7/2000 | Madsen et al. |
| 6,413,227 B1 | 7/2002 | Yost et al. |
| 6,702,743 B2 | 3/2004 | Michaeli |
| 2003/0191410 A1 | 10/2003 | Yost et al. |
| 2004/0087871 A1 | 5/2004 | Ragauskas |
| 2009/0287084 A1 | 11/2009 | Daubaris et al. |
| 2018/0279877 A1 | 10/2018 | Berdahl et al. |
| 2019/0069876 A1 | 3/2019 | Michaeli et al. |

OTHER PUBLICATIONS

Khan MN, Shallwani H, Khan MU, Shamim MS. Noninvasive monitoring intracranial pressure—A review of available modalities. Article. Apr. 5, 2017. 11 pages.

Cerepress and Vittamed 205 for non-invasive intracranial pressure measurement. Article Mar. 2015. 4 pages.

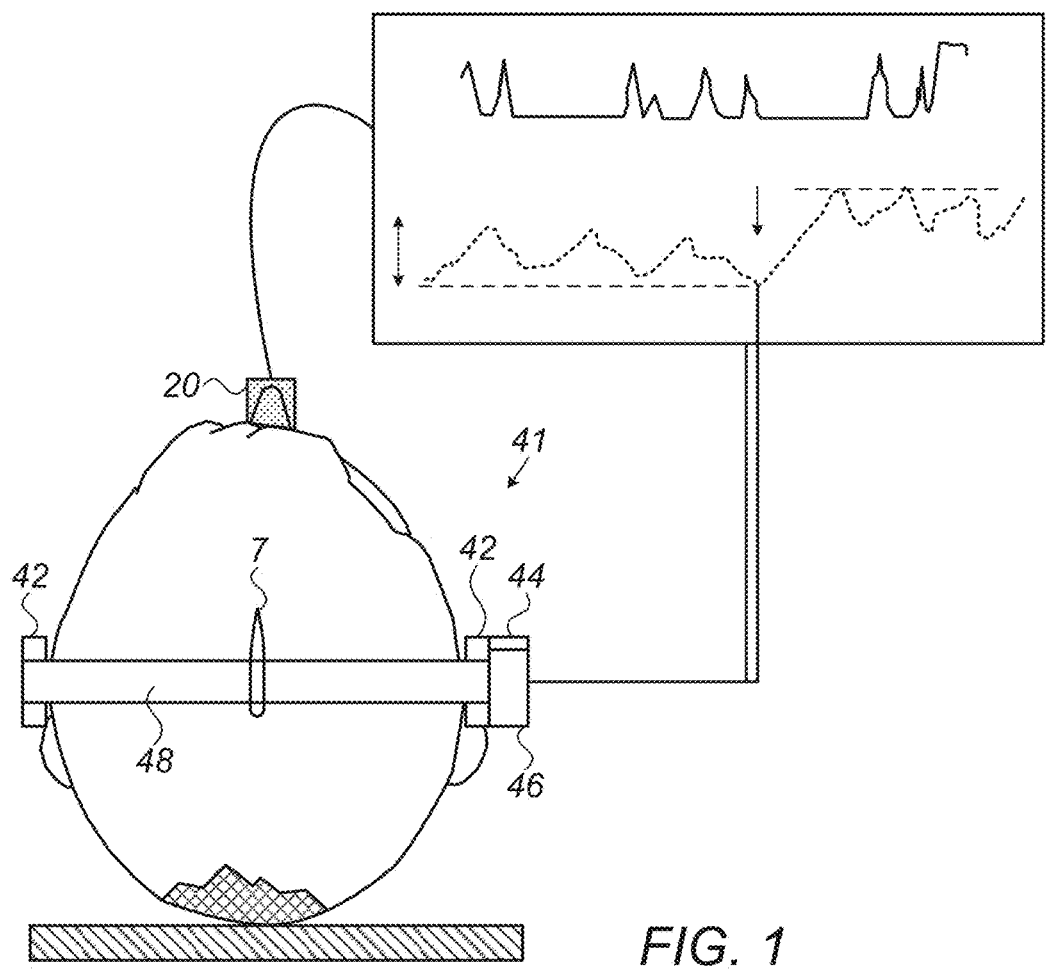
FIG. 1
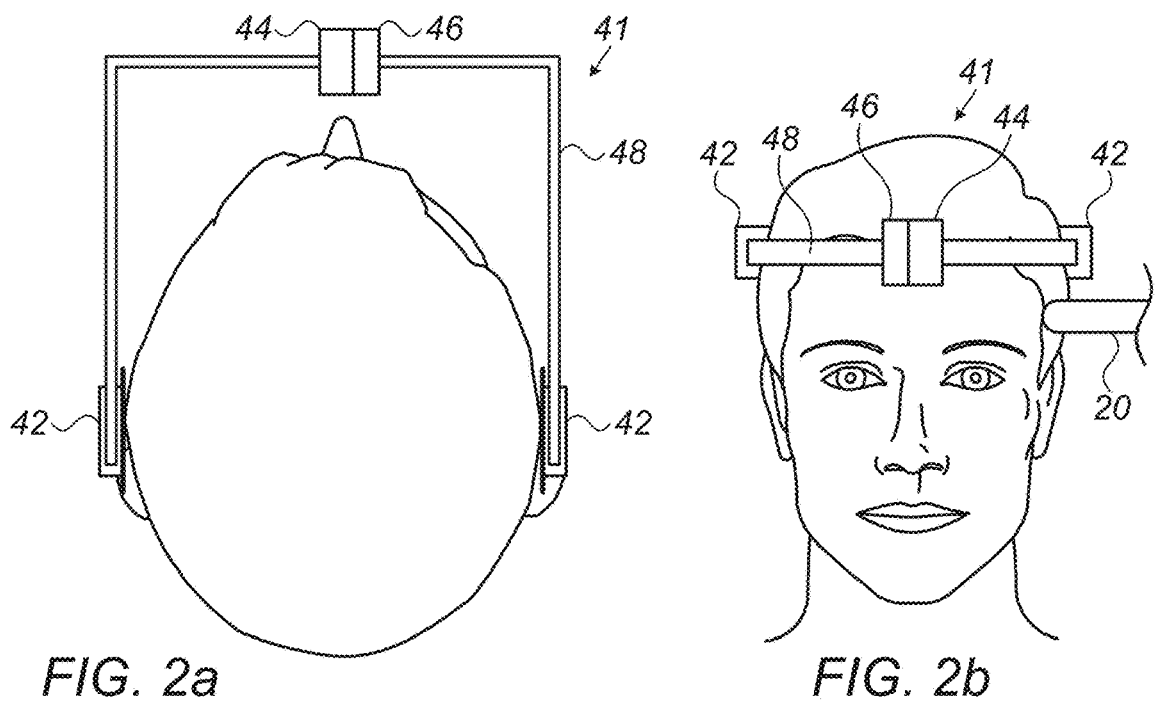
FIG. 2a
FIG. 2b

METHOD AND APPARATUS FOR NONINVASIVE ABSOLUTE (MEAN) INTRACRANIAL PRESSURE (A-ICP) MEASUREMENT AND/OR MONITORING

FIELD AND BACKGROUND OF THE INVENTION

The invention relates to apparatuses and methods for measuring the intracranial pressure (ICP), such as a mean ICP or absolute ICP or absolute mean intracranial pressure (ICP), of a mammalian subject, for example a person, noninvasively.

Standard methods for measuring intracranial pressure (ICP) involve drilling a hole through the skull and inserting an intraventricular catheter, subdural screw, or epidural sensor operatively connected to an external pressure sensor or transducer. These invasive methods cannot always be employed when desired or needed because they generally require a neurosurgeon to carry them out, are expensive to perform, and present risk of complications to the patient. It should also be plainly apparent as a matter of common sense that having to cut a patient's head open is a less desirable manner of obtaining an important parameter (intracranial pressure (ICP)) than obtaining the parameter without having to cut the patient's head open at all. There are limits to how often you can cut the patient's head open.

In order to overcome the problems of the invasive methods and to make ICP measuring more readily available considerable effort has been invested in devising non-invasive methods and devices of measuring ICP. U.S. Pat. Nos. 5,951,477 and 8,926,515 describe an ultrasonic Doppler device which detects the pulsatility indexes of the blood flow inside the eye artery for both intracranial and extracranial eye artery portions. The eye in which the blood flow is monitored is subjected to a small pressure, sufficient to equalize the pulsatility index measurements of the internal and external portions of the eye artery. The pressure at which such equalization occurs is used as a reference for autocalibration of the apparatus so that continuous absolute intracranial pressure measurements may be taken over a particular sampling period.

This method has a great number of drawbacks and limitations. One is that it does not take into account that pressure to the eye globe causes mechanical irritation of eyes. As a result, an autonomous sympathetic apparatus of eye globs will cause reflector Cerebral Vascular Spasm (CVS), which in turn causes inaccuracy in the absolute ICP measurement, such that the results obtained do not exactly describe the real ICP. This is especially the case with the 80% of traumatic brain injury (TBI) patients that suffer from cerebral vasospasm (CV). Second, a great deal of inaccuracy is generated using this method because iatrogenic cerebral vascular spasm (CVS) after depression of the eye globe and closing of the superior and inferior ophthalmic and vortices retrobulbar veins, causes reduction of venous output from the eye globe to the intracranial space (Cavernous sinus).

Third, the results of transorbital dopplerography of ophthalmic arteries are variable and they depend on the operator and variability of anatomical features of each individual. Repeatability and reliability of dopplerography is very low.

Fourth, between 10% and 25% of patients with traumatic brain injury suffer from bilateral or unilateral periorbital ecchymosis, sub skin hemorrhages, sub skin facial-orbital emphysema, and orbital bone fractures and it is impossible to use the above mentioned method on these patients. For patients in intensive care units suffering from severe brain injury with elevated ICP from 20 to 60 mmHg, the accuracy of this method is low and impractical for wide use. Noninvasive ICP measurement as described in U.S. Pat. Nos. 5,951,477 and 8,926,515, to the extent that it can be used at all, can most probably be used only on healthy individuals.

Applicant is not aware of any widely used noninvasive method or apparatus for ICP monitoring or measurement. An article in Surgical Neurology International by Khan, Marium Naveed et al. published 5 Apr. 2017 entitled "Noninvasive monitoring intracranial pressure—A review of available modalities" reviewed 196 professional articles discussing 15 different noninvasive modalities and concluded that "there is still no noninvasive ICP monitoring modality available to replace the invasive techniques" after summarizing the situation as follows (citations omitted): "Intracranial pressure (ICP) is defined as the pressure inside the skull, and therefore, the pressure inside the brain tissue and the cerebrospinal fluid (CSF) . . . . Normal ICP is usually considered to be 5-15 mmHg in a healthy supine adult, 3-7 mmHg in children, and 1.5-6 mmHg in infants. ICP>20 mmHg is considered to be elevated, and this is considered an important cause of secondary injury leading to irreversible brain injury and death. ICP monitoring is used in a number of conditions; traumatic brain injury, intracerebral hemorrhage, subarachnoid hemorrhage, hydrocephalus, malignant infarction, cerebral edema, CNS infections, hepatic encephalopathy, to name a few, and in all of these conditions ICP monitoring in the light of other parameters can influence management for better outcomes. There are several conditions where it is important to monitor ICP, as even minor fluctuations may require a change in management. The gold standard for monitoring ICP is an intraventricular catheter connected to an external pressure transducer; the catheter is placed into one of the ventricles through a burr hole. The catheter can also be used for therapeutic CSF drainage and for administration of drugs. Even though it remains an accurate and cost-effective method of ICP monitoring, it is associated with a number of complications. These include risk of infection, hemorrhage, obstruction, difficulty in placement, malposition, etc. Other invasive modalities for ICP monitoring, all of which entail the same complications as intraventricular catheter insertion, include intraparenchymal monitors, subdural, and epidural devices, as well as lumbar puncture measurements. Due to the number of complications associated with invasive ICP monitoring, researchers and clinicians have been trying to develop a reliable noninvasive modality for ICP monitoring. From the use of the Fontogram in the 1970s, to the ongoing experiments on acoustoelasticity effects on ICP, there is still no noninvasive ICP monitoring modality available to replace the invasive techniques."

SUMMARY OF THE INVENTION

Certain embodiments of the invention take into account venous and cerebro-spinal fluid (CSF) output from the skull and measure local pressures in (Intra Parenchymal Pressure) IPP, (Intra Ventricular Pressure) IVP, supra and subtentorial compartments Pressure (SUPTP, SUBTP), ICRS capacity which increases the accuracy, reliability and repeatability of the ICP measurements. In contrast, the method disclosed in U.S. Pat. Nos. 5,951,477 and 8,926,515 does not take into account venous and cerebro-spinal fluid (CSF) output from the skull and does not make measurements of local pressures in (Intra Parenchymal Pressure) IPP, (Intra Ventricular Pressure) IVP, Supra and Subtentorial compartments Pressure (SUPTP, SUBTP) or ICRS capacity.

One aspect of the invention is a non-invasive method for measuring an intracranial pressure (ICP) of a person, comprising using at least one probe configured to be positioned so as to emit energy at pulsating tissue or cavities in the brain of the person and to receive reflected signals; deriving from the signals or from images associated with the signals, using a processor, an ICP waveform; applying an external pressure, and then incrementally increasing the external pressure, to the person's skull using a pressure mechanism in communication with the processor, the pressure mechanism including a pressure applying component having at least one surface and a manometer and configured to apply the external pressures including the incrementally increased external pressures, to the person's skull when the at least one surface contacts the person's skull; detecting, using the processor, a decrease in amplitude of the ICP waveform, the decrease beginning at an initial value A1 of the amplitude, and a final value A2, detecting, using the processor, an intracranial reserve space (ICRS); intermediate period and detecting such decrease in amplitude of the ICP waveform that occurs after the ICRS intermediate period is completed; and determining, using the processor, the ICP of the person as a function of values of the applied external pressures applied beginning on or after a time of the initial value A1 and ending by a time of the final value A2 or earlier, wherein the values of the applied external pressures include the values of the applied incrementally increased external pressures.

In some embodiments, one of the following is true: (i) the final value A2 is a value at which the amplitude reaches a predefined absolute or relative amount with additional increase in applied external pressure and the processor is configured to determine the ICP from a sum of the value of the applied external pressures, (ii) the final value A2 is a value to which the amplitude has decreased from the initial value A1 such that at the final value the amplitude is moving towards but has not yet reached the amplitude that is the predefined absolute or relative amount with additional increase in applied external pressure, and the processor is configured to determine the ICP or an estimated ICP by extrapolating the sum to a point at which the amplitude reaches the predefined absolute or relative amount with additional increase in applied external pressure.

In some embodiments, the method further comprises using the processor to perform image processing algorithms that measure at least one of the following: changes in a baseline, the value of the amplitude, phase shifts, and resonance frequency, of the ICP waveform.

In some embodiments, the method further comprises using the processor to perform image processing algorithms that measure at least two of the following: changes in a baseline, the value of the amplitude, phase shifts, and resonance frequency, of the ICP waveform.

In some embodiments, the method further comprises using the processor to perform image processing algorithms that measure at least three of the following: changes in a baseline, the value of the amplitude, phase shifts, and resonance frequency, of the ICP waveform.

In some embodiments, the method further comprises applying the energy using a steerable one-dimensional ultrasound probe placed on a forehead of the person and focused on an area in the brain where the pulsations occur. In some embodiments, the one-dimensional ultrasound probe is configured to operate at a frequency of 0.5-1.5 MHz. In some embodiments, the area in the brain is at least one of: the third ventricle, lateral ventricles, thalamic striate veins and central cerebral veins of the 3rd ventricular cavity, edges of the 3rd and lateral ventricles, 4th ventricle, choroid plexus veins of ventricles, and cortical pulsations. In some embodiments, the signals are registered on the sagittal plane 20-50 degrees to the horizontal (axial) plane.

In some embodiments, the method further comprises applying the energy using a steerable two-dimensional USB ultrasound probe configured to be attached to a temporal region of the head or attached so as to obtain at least one of (i) an axial slice, (ii) a coronal slice, (iii) an oblique slice, the two-dimensional probe focused on an area in the brain where pulsations of the one or more of brain tissue, brain vessels and brain ventricles occur. In some embodiments, the two-dimensional ultrasound probe is configured to operate at a frequency of 1.5-2.5 MHz. In some embodiments, the area in the brain is one of the following: the edges of the third ventricle, the cerebral central vein, and the thalamic striate veins.

In some embodiments, the external pressure is applied on each side of the person's head in a bi-temporal direction or in a coronal, axial or oblique direction.

In some embodiments, the method further comprises using the processor to derive the ICP waveform from the signals using a fast Fourier transform performed on the signals derived from the pulsating tissue or cavities in the brain to obtain a distribution of resonance frequencies in a spectrum.

In some embodiments, the method further comprises using the processor to perform an inverse Fourier transform to produce noninvasive ICP waveforms of the pulsating tissue or cavities.

In some embodiments, the method further comprises positioning the at least one probe adjacent the person's head, wherein the probe is configured to emit ultrasound energy and wherein the ICP waveform has variations that correspond to the pulsating tissue or cavities in the brain.

Another aspect of the invention is an apparatus for non-invasive measurement of an intracranial pressure (ICP) of a person, comprising at least one probe configured to be positioned so as to emit energy at pulsating tissue or cavities in the brain and to receive reflected signals; a processor configured to derive from the signals or from images associated with the signals an ICP waveform; and a pressure mechanism, including a pressure applying component having at least one surface and a manometer, in communication with the processor configured to apply an external pressure to the person's skull using the at least one surface of the pressure mechanism, wherein the processor is configured to detect a decrease in amplitude of the ICP waveform, the decrease beginning at an initial value A1 of the amplitude, and to detect a final value A2, wherein the processor is configured to detect an intracranial reserve space (ICRS) intermediate period and to detect such decrease in amplitude of the ICP waveform that occurs after the ICRS intermediate period, wherein the processor is configured to determine the ICP of the person as a function of values of the applied external pressure applied beginning on or after a time of the initial value A1 and ending by a time of the final value A2 or earlier.

In some embodiments, the pressure mechanism is configured to incrementally increase the external pressure before the processor detects the final value of the amplitude.

In some embodiments, the at least one probe is a steerable one-dimensional ultrasound probe configured to be placed on a forehead of the person and focused on an area in the brain where pulsations of the brain tissues occur. In some embodiments, the one-dimensional ultrasound probe is configured to operate at a frequency of 0.5-1.5 MHz. In some embodiments, the signals are registered on the sagittal plane 20-50 degrees to the horizontal (axial) plane.

In some embodiments, the at least one probe is a steerable two-dimensional USB ultrasound probe configured to be attached to a temporal region of the head or attached so as to obtain at least one of (i) an axial slice, (ii) a coronal slice, (iii) an oblique slice, the two-dimensional probe focused on an area in the brain where pulsations of the one or more of brain tissue, brain vessels and brain ventricles occur. In some embodiments, the two-dimensional ultrasound probe is configured to operate at a frequency of 1.5-2.5 MHz. In some embodiments, the area in the brain is one of the following: the edges of the third ventricle, the cerebral central vein, and the thalamic striate veins.

Another aspect of the invention is a non-invasive method for measuring a mean intracranial pressure (ICP) of a person, comprising using at least one probe positioned adjacent an exterior tissue layer of the person's head to emit energy at pulsating one or more of brain tissue, brain vessels and brain ventricles in the head and to receive reflected signals; deriving from the signals or from images associated with the signals, using a processing unit, an ICP waveform having a discernable amplitude whose variations correspond to the pulsating one or more of brain tissue, brain vessels and brain ventricles; applying external pressure to an outer surface of the head using a pressure mechanism in communication with the processing unit, the mechanism including a pressure applicator, by applying an initial external pressure and then incrementally increasing the external pressure to the outer surface using the applicator; after a decrease in amplitude of the ICP waveform, the decrease beginning at an initial value A1 of the amplitude, (in some embodiments the processing unit also instructing the pressure mechanism to halt application of the external pressure when the amplitude reaches a final value A2) determining, by the processing unit, the ICP of the person from a sum, or an extrapolated sum, of applied external pressures applied beginning on or after a time of the initial value A1 and ending by a time of the final value A2, wherein one of the following is true: (i) the final value is a value at which the amplitude remains stable with additional increase in applied external pressure and the processing unit is configured to determine the ICP from the sum of applied external pressures, (ii) the final value A2 is a value to which the amplitude has decreased from the initial value A1 such that at the final value the amplitude is moving towards but has not yet reached the amplitude that remains stable with additional increase in applied external pressure, and the processing unit is configured to determine the ICP or an estimated ICP by extrapolating the sum to a point at which the amplitude remains stable with additional increase in applied external pressure.

In some embodiments, the energy is applied using a steerable one-dimensional ultrasound probe placed on a forehead of the person and focused on an area in the brain where the pulsations occur. In some embodiments, the one-dimensional ultrasound probe is operated at a frequency of 0.5-1.5 MHz. In some embodiments, the area in the brain is at least one of the following: the third ventricle, lateral ventricles, thalamic striate veins and central cerebral veins of the 3rd ventricular cavity, edges of the 3rd and lateral ventricles, 4th ventricle, choroid plexus veins of ventricles, and cortical pulsations.

In some embodiments, the signals are ultrasound signals that are registered on the sagittal plane 20-50 degrees to the horizontal (axial) plane.

In some embodiments, wherein the energy is applied using a steerable two-dimensional (2D) ultrasound probe attached to a temporal region of the head or attached so as to obtain at least one of (i) an axial slice, (ii) a coronal slice, (iii) an oblique slice, the two-dimensional probe focused on an area in the brain where pulsations of the one or more of brain tissue, brain vessels and brain ventricles occur. In some embodiments, the two-dimensional US probe is operated at a frequency of 1.5-2.5 MHz. In some embodiments, the area in the brain is one of the following: the edges of the third ventricle, the cerebral central vein, and the thalamic striate veins.

In some embodiments, the external pressure is applied in uniform stepwise increments.

In some embodiments, the external pressure is applied on each side of the person's head in a bi-temporal direction.

In certain embodiments, the processing unit is configured to extrapolate the sum using a ratio between A1 and a difference between A1 and A2 taking into consideration how many times external pressure was applied from the time of A1 to the time of A2.

In certain embodiments, deriving the ICP waveform from the ultrasound signals is accomplished by a fast Fourier transform performed on the signals derived from the pulsations of the one or more of brain tissue, brain vessels and brain ventricles in the area of the brain where pulsations of the brain tissue occur to obtain a distribution of the resonance frequencies in a spectrum and wherein an inverse Fourier transform is also performed to reconstruct the non-invasive ICP waveform from the pulsations.

Another aspect of the invention is an apparatus for non-invasive measurement of mean intracranial pressure (ICP) of a person, comprising at least one probe configured to be positioned adjacent an exterior tissue layer of the person's head and to emit energy at pulsating one or more of brain tissue, brain vessels and brain ventricles of the person's head and to receive reflected signals; a processing unit configured to derive from the signals or images associated with the signals an ICP waveform whose variations correspond to the pulsating one or more brain tissue, brain vessels and brain ventricles; a pressure mechanism in communication with the processing unit configured to apply an external pressure to an outer surface of the head by applying an initial external pressure and then incrementally increasing the external pressure applied to the outer surface, wherein the processing unit is configured to detect a decrease in amplitude of the ICP waveform, the decrease beginning at an initial value A1 of the amplitude, and to detect a final value A2, the processing unit is configured to determine the ICP of the person from a sum of applied external pressures applied beginning on or after a time of the initial value A1 and ending by a time of the final value A2, wherein one of the following is true: (i) the final value is a value at which the amplitude remains stable with additional increase in applied external pressure and the processing unit is configured to determine the ICP from the sum of applied external pressures, (ii) the final value A2 is a value to which the amplitude has decreased from the initial value A1 such that at the final value the amplitude is moving towards but has not yet reached the amplitude that remains stable with additional increase in applied external pressure, and the processing unit is configured to determine the ICP or an estimated ICP by extrapolating the sum to a point at which the amplitude remains stable with additional increase in applied external pressure.

In some embodiments, the at least one probe comprises an ultrasound probe configured to emit ultrasound energy and to receive ultrasound signals. In some embodiments, the ultrasound probe is configured to generate energy gradients between emitted and reflected ultrasound signals.

In some embodiments, the processing unit is configured to perform image processing algorithms that measure at least three of the following: changes in the baseline, the value of the amplitude, phase shifts, and resonance frequency, of the ICP waveform.

In some embodiments, the at least one probe is a steerable one-dimensional ultrasound probe configured to be placed on a forehead of the person and focused on an area in the brain where pulsations of the brain tissues occur. In some embodiments, the one-dimensional ultrasound probe is configured to operate at a frequency of 0.5-1.5 MHz. In some embodiments, the area in the brain is at least one of: the third ventricle, lateral ventricles, thalamic striate veins and central cerebral veins of the 3rd ventricular cavity, edges of the 3rd and lateral ventricles, 4th ventricle, choroid plexus veins of ventricles, and cortical pulsations.

In some embodiments, the at least one probe is a steerable two-dimensional USB ultrasound probe configured to be attached to a temporal region of the head and focused on an area in the brain where pulsations of the brain tissues, brain vessels and brain ventricles occur or attached so as to obtain at least one of (i) an axial slice, (ii) a coronal slice, (iii) an oblique slice, the two-dimensional probe focused on an area in the brain where pulsations of the one or more of brain tissue, brain vessels and brain ventricles occur. In some embodiments, the two-dimensional ultrasound probe is configured to operate at a frequency of 1.5-2.5 MHz. In some embodiments, the area in the brain is one of the following: the edges of the third ventricle, the cerebral central vein, and the thalamic striate veins.

In some embodiments, the signals are registered on the sagittal plane 20-50 degrees to the horizontal (axial) plane.

In some embodiments, the external pressure is applied in uniform stepwise increments.

In some embodiments, the external pressure is applied on each side of the person's head in a bi-temporal direction or in a coronal, axial or oblique direction.

In some embodiments, the pressure mechanism comprises one of the following: (a) a pressure applicator that includes an inflatable sleeve applied to the person's head or (b) a helmet configured to apply pressure at specific locations on the skull of the person.

In some embodiments, the processing unit is configured to extrapolate the sum using a ratio between A1 and a difference between A1 and A2 taking into consideration how many times external pressure was applied from the time of A1 to the time of A2.

In some embodiments, the processing unit is configured to derive the ICP waveform from the ultrasound signals by a fast Fourier transform performed on the brain pulsations in the area of the brain where pulsations of the brain tissue occur to obtain a distribution of the resonance frequencies in the spectrum and wherein an inverse Fourier transform is performed to reconstruct the noninvasive ICP waveform(s) of the brain pulsations.

A still further aspect of the invention is an apparatus for non-invasive measurement of mean intracranial pressure (ICP) of a person, comprising at least one probe configured to be positioned adjacent the person's head and to emit energy at pulsating tissue or cavities in the brain (or head) and to receive reflected signals; a processing unit configured to derive from the signals or from images associated with the signals an ICP waveform; a pressure mechanism in communication with the processing unit and configured to apply an external pressure to an outer surface of the head and to measure the applied external pressure, wherein the processing unit is configured to detect a decrease in amplitude of the ICP waveform, the decrease beginning at an initial value A1 of the amplitude, and to detect a final value A2, wherein the processing unit is configured to determine the ICP of the person either from a sum of applied external pressures applied beginning on or after a time of the initial value A1 and ending by a time of the final value A2, or from an extrapolated sum of applied external pressures. In some embodiments, the processing unit is configured to detect an ICRS intermediate period and to such decrease in amplitude of the ICP waveform that occurs after the ICRS intermediate period is completed. In some embodiment, when the amplitude reaches the final value, the processing unit is configured to also communicate to the pressure mechanism to halt external pressure. In certain embodiments of the invention, mean ICP (sometimes referred to as "M-ICP") is obtained in a reliable manner noninvasively and with an accuracy that is comparable to the "gold" standard of ICP measurement, namely the invasive measurement. In some embodiments of the invention, the noninvasive ICP of a person can be measured repeatedly instead of having to wait a certain number of days, which is what the neurosurgeon must do between invasive measurements of ICP. The invention also avoids any surgery on the patient's head. In certain embodiments, the invention also widens the applicability of ICP measurement even relative to the invasive measurement of ICP because the invention can be utilized even for people whose score on the Glasgow Coma Scale (GCS) is too low to allow an invasive ICP measurement according to current medical practice protocol (i.e. less than about 8).

Furthermore, in certain embodiments, the mean ICP measurement measured by the invention is more accurate than other methods and devices because in certain embodiments it takes into consideration the intracranial reserve space (ICRS) of the patient in the sense that the processing unit determines the noninvasive ICP measurement by adding together the applied external pressure amounts during a period of time after a decline in amplitude of ICP waves and this period of time occurs only after any effect caused by spare intracranial reserve space (ICRS) within the subject's skull. As shown in FIG. 7, the effect of having spare ICRS capacity means that after a crisis point where some resistance is overcome and some tissue deformation begins to occur, in many or most patients, there is an intermediate period during which ICP waveform amplitude is relatively level compared to before and immediately after the intermediate period and during which the ICP value initially increases and then decreases and after the intermediate period the ICP vale more markedly increases. This intermediate period (sometimes referred to herein as the "ICRS intermediate period" or the "ICRS occupied intermediate period") during which the amplitude of the ICP waveform is relatively level or flat is due to the effect of spare ICRS capacity that the person has in their skull. What happens during this ICRS intermediate is that the body's own compensatory mechanism moves the cerebrospinal fluid (CSF) of the person from the intracranial space to an intraspinal space or to a spinal channel space, thereby reducing the intracranial pressure of the person. The fact that the invention, in accordance with certain embodiments, takes that spare ICRS capacity (intracranial reserve space) into consideration by configuring the processing unit 30 to only calculate the sum (or extrapolated sum) of applied external pressures during a period after the potential influence of the ICRS capacity (i.e. after the ICRS intermediate period), meaning after the body's compensatory mechanism has acted (if it was able to act meaning assuming there was intracranial reserve space to begin with), makes the invention's ICP measurement more accurate. Many attempts to measure ICP, whether invasive or non-invasive are inaccurate because they do not take into consideration ICRS capacity.

Certain embodiments of the method and apparatus of the invention are capable of reliable measurement of a person's ICP noninvasively for a very wide range of patients in need of ICP measurement or monitoring including and not limited to those with subskin hemorrhage, those with fracture of skull base and those with CSF leak.

"Simulated ICP" or "simulation of ICP" as used herein (including in FIG. 7) refers to an estimate of a person's expected ICP after application of each magnitude of outside pressure on the person's head applied in accordance with certain embodiments of the invention.

These and other features, aspects and advantages of the invention will become better understood with reference to the following drawings, descriptions and claims.

BRIEF DESCRIPTION OF THE DRAWINGS

Various embodiments are herein described, by way of example only, with reference to the accompanying drawings, wherein:

FIG. 1 is a top view that schematically shows an apparatus including an ultrasound probe, a mechanism for applying external pressure to the skull for noninvasive measurement of A-ICP and a digital ICP waveform, according to an embodiment of the invention;

FIG. 2A is a top view schematically showing a mechanism for applying external pressure to the skull of a person for noninvasive measurement of the A-ICP according to an embodiment of the invention;

FIG. 2B is a front view schematically showing a mechanism for applying external pressure using different points of contact from that shown in FIG. 2A, in accordance with an embodiment of the invention;

DETAILED DESCRIPTION OF THE INVENTION

Figure 3:
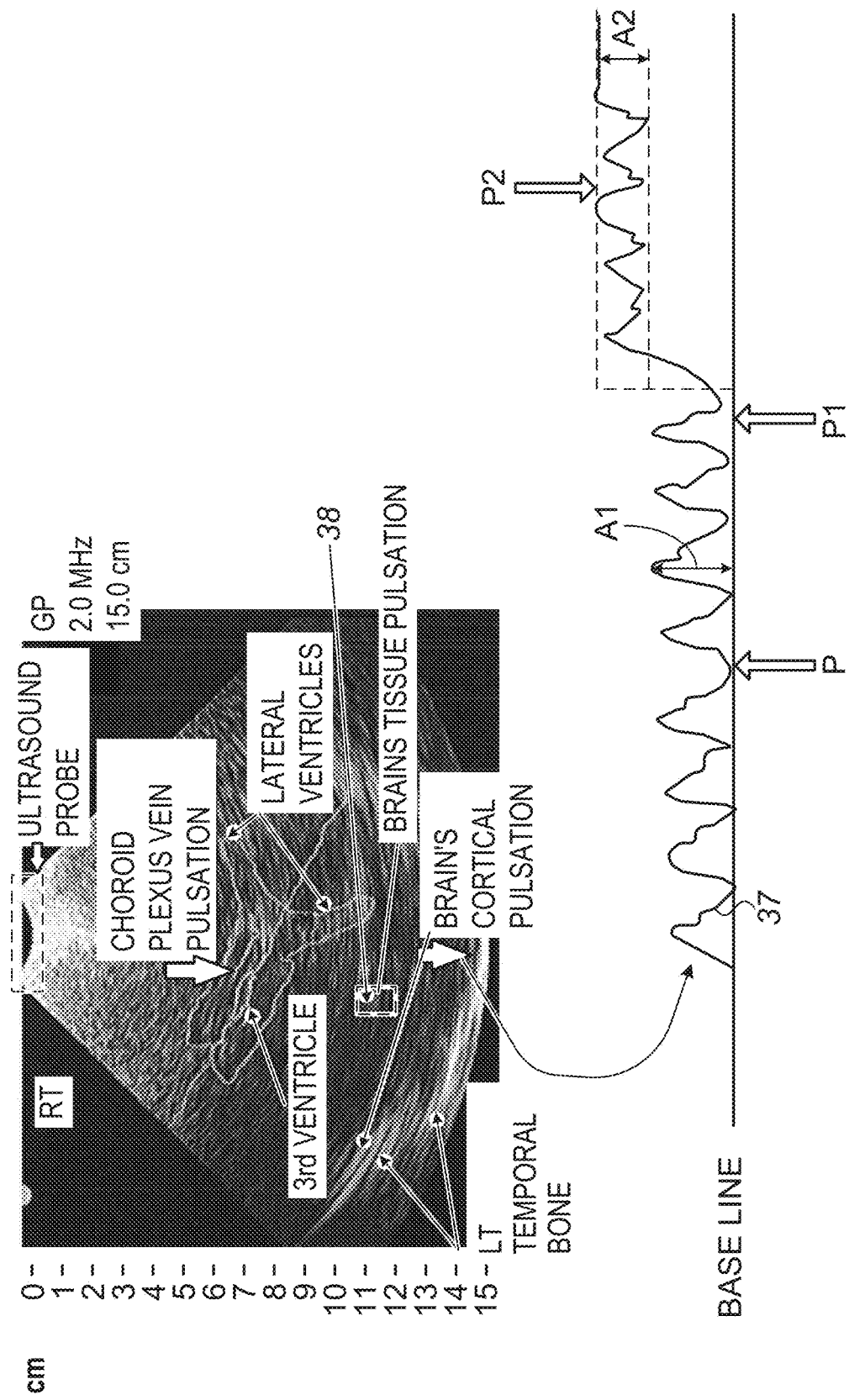
FIG. 3 shows an ultrasound image arising from use of a 2-D ultrasound probe and shows an ICP waveform derived from this image using a processing unit, in accordance with an embodiment of the invention.

The following detailed description is of the best currently contemplated modes of carrying out the invention. The description is not to be taken in a limiting sense, but is made merely for the purpose of illustrating the general principles of the invention, since the scope of the invention is best defined by the appended claims.

The invention generally provides an apparatus and method of measuring and/or monitoring absolute intracranial pressure ICP of a person noninvasively (sometimes referred to as "(A)ICP"). This refers to the fact that while the ICP values are in theory dependent on the atmospheric pressure, the invention ignores variability in atmospheric pressure since such changes in atmospheric pressure are typically negligible. In certain embodiments, normal atmospheric pressure (760+−mm. Hg.) is treated as if it is zero and the ICP measurement is not dependent on the atmospheric pressure.

In some embodiments, the invention provides an apparatus and method of measuring and/or monitoring mean intracranial pressure ICP of a person noninvasively over time (albeit in certain embodiments a brief period of time). Accordingly, mean ICP may be the person's ICP derived from measurements taking place over as short a time as a few seconds and up to several hours or longer. In some cases, several such noninvasive ICP measurements are taken (with a hiatus between each one) and they are averaged together to obtain one mean ICP over the entire time period. However, in the case of mean ICP measurement that is continuous (without a hiatus), the range of time is approximately a few seconds to approximately one to two minutes and this one measurement represents the mean ICP. For ICP measurements that include one or more hiatuses, such mean ICP measurements can extend for several hours since one is averaging the results of several measurements taken during this time period where each measurement may have taken place over 2-3 seconds or longer (up to about 2 minutes). In general, monitoring of the ICP of a person may be performed using certain embodiments of the method and apparatus of the invention for as long a period as desired and the ICP measurements of the same person may be repeated at intervals shorter than a day and even shorter than an hour. Accordingly, in certain embodiments the invention achieves recurrent monitoring or repeated monitoring of ICP noninvasively accurately and reliably. In certain embodiments, the ICP (or mean ICP) is noninvasively monitored or measured every hour, every half hour, every quarter hour or every 10 minutes or every 5 minutes for days, weeks or months.

The invention in certain embodiments is a non-invasive method of measurement of absolute intra cranial pressure ((A)ICP) for example in patients with severe brain injury due to traumatic brain injury (TBI), brain swelling, or other intracranial space occupying lesions (SOL) such as ischemic and hemorrhagic stroke, brain tumors, unconscious patients of unknown etiology, and healthy or conscious patients. The invention is based on an unexpected observation by one of the inventors that, contrary to the conventional wisdom in the art, moderate external pressure applied to the skull that does not cause the patient pain, causes micron-size local deformation of the skull bones and effects changes in the amplitude of the noninvasive intracranial pressure (ICP) waves. The invention in certain embodiments incorporates imaging techniques, for example ultrasound imaging techniques, for observation of motions (pulsations), for example multiaxial, volumetric motions, of brain tissue and brain ventricles, brain arteries and veins that in some embodiments are caused by the ultrasound energy gradients between emitted and received by an ultrasound transducer, in contact with the exterior soft tissue layer or skull of a patient's head. In certain embodiments, the invention allows real time imaging of vertical pulsatility of brain tissues, edges of brain's ventricles and brain's vessels (arteries and veins) inside the tissues and ventricles cavities of the brain.

The invention in some embodiments derives a waveform from signals or images associated with the signals received as a result of at least one probe, for example ultrasound images produced from emitting and receiving signals using for example a one-dimensional or two-dimensional probe (or both for example simultaneously), on the person's skull. In some embodiments, the waveform (which is referred to herein as an ICP waveform) is derived (and displayed) by a processing unit at the same time that the at least one probe is being used to emit energy receive reflected signals and images and while external pressure, for example intermittent external pressure, is applied to the person's skull, for example in stepwise increments.

The amplitude of the waveform and its decline is used in some embodiments by the processing unit (or alternatively by an observer) to determine which applied pressures to use in using a sum of applied pressures to derive the intracranial pressure of the person (and to determine when to terminate application of the external pressure on the person's skull), i.e. the beginning point and the endpoint of the applied pressures used in calculating the ICP value. Furthermore, other characteristics of the ICP waveform such as a baseline shift (for example an increase in the baseline) or shift in phase of the amplitude relative to the baseline (i.e. going below the baseline as opposed to above the baseline) are used in some embodiments by the processing unit to determine or confirm the beginning point of the applied pressures to use in the ICP value calculation.

For example, the decline in the amplitude to a zero or negligible or near negligible amount results in some embodiments in halting application of the external pressure. In another example, the decline in the amplitude by a significant amount such as by more than 75% or by more than 90% or by more than 95% or by 95% to 99% results in some embodiments in halting application of the external pressure. In some embodiments, the decline in amplitude sufficiently to be able to extrapolate a further decline in amplitude such that the total decline in amplitude is by a significant amount or to a zero or negligible or near negligible amount, results in halting application of the external pressure.

In certain embodiments of the invention, the decline in amplitude is used to trigger an instruction to halt application of the external pressure only when this decline takes place after certain physiological phenomena have occurred, namely a deformation of tissue in the skull and typically a change in the baseline of the ICP waveform.

The pulsations of the tissue and/or ventricles in the brain may be said to arise from the intracranial pressure and from the heart rhythm of the person. The amplitude of these brain tissue pulsations, may be recorded on a graph as a waveform, and this waveform is then referred to herein as an ICP waveform or ICP waveforms. Note for comparison purposes that when invasive ICP measurements are conducted by drilling a hole through the skull and inserting an intraventricular catheter, subdural screw, or epidural sensor, such measurements yield both an ICP wave that shows the variability in the ICP as well as a scalar magnitude or value representing the person's intracranial pressure (over time). In contrast, the ICP waveform derived from the ultrasound images herein shows the variability of the ICP but lacks a scalar (or other) magnitude or value representing the intracranial pressure of the person (over time or even at a given point in time) associated with it. Accordingly, the term "ICP waveform" as used herein is not and does not refer to the actual intracranial pressure values of the person measured, for example invasively (or otherwise) over time or at a moment. However, the invention, in certain embodiments described herein, combines this ICP waveform with externally applied pressure to the skull and a processing unit to creatively derive intracranial pressure values (for example scalar values representing the magnitude of the intracranial pressure of the person) that are in certain embodiments as accurate as the invasively measured ICP values.

In certain embodiments, the invention noninvasively measures intracranial pressure of a person, for example mean ICP, in a manner that is not dependent on the angle of ultrasound insonation. In certain embodiments, the energy from the probe of the invention is able to noninvasively penetrate the skull of 99% of patients. In certain embodiments, the invention noninvasively measures intracranial pressure of a person, for example mean ICP, in a manner that is not dependent on the skill or accuracy of a technician or operator of the apparatus 10 or method 100 of the invention. These factors increase the reliability and repeatability of the method 100 and apparatus 10 of the invention in certain embodiments. Use of dopplerography and ultrasound with frequency gradients, in contrast, would generate ICP measurement results that depend on the skill of the operator and on the angle of insonation and hence have low repeatability and low reliability.

The principles and operation of a Method and Apparatus for Noninvasive Absolute (Mean) Measurement and/or Recurrent Monitoring of Intracranial Pressure (A-ICP) may be better understood with reference to the drawings and the accompanying description.

As shown in FIGS. 1-9 and 11-12, in one embodiment, the invention is an apparatus 10 for non-invasive measurement (and/or recurrent monitoring) of mean intracranial pressure (ICP) of a person. In embodiments in which the processing unit 30 or another part of the apparatus is remote from other elements of apparatus 10, the apparatus can also be referred to as a system 10.

In some embodiments, as shown in FIG. 1, apparatus 10 includes at least one probe 20 positioned or configured to be positioned adjacent an exterior tissue layer, typically a soft exterior tissue layer, of the person's or subject's head. Probe may be an ultrasound probe, or in other embodiments a probe that generates other forms of energy for example energy waves that are microwave, radio waves, near infra red wave radiation or terahertz waves, that are directed at the pulsating at least one of brain tissue, brain vessels and ventricles in the head of the person. The at least one probe is configured to receive reflected signals and/or images associated with the reflected signals.

The following discussion discusses a non-limiting implementation of the invention using ultrasound probe 20 but it should be understood that the below discussion is also applicable to probes that emit and recited reflected signals of other forms of energy. In certain embodiments, the at least one probe 20 is an ultrasound probe 20 that is configured in some embodiments to emit ultrasound energy at pulsating at least one of brain tissue, brain vessels and ventricles in the head. In certain embodiments, the at least one ultrasound probe 20 is configured to create ultrasound energy gradients for example between energy of emitted and reflected ultrasound signals. In some embodiments, the at least one probe 20 is configured to effectuate digital (in some cases "real time") tracking of these brain tissues, vessels and/or ventricles to create noninvasive ICP waveforms. In certain embodiments, the ICP waveform(s) generated invasively is similar or equivalent in variability to ICP waves that are derived invasively. The at least one probe 20 may be further configured to receive ultrasound signals that bounce off the tissue and/or ventricles and are received by the at least one probe 20. In some embodiments the at least one probe is configured to track pulsations of different localization, different brain tissue volume and/or different directions (i.e. multi-axial pulsation or brain volumetric pulsation). In certain embodiments, the at least one probe 20 is in communication with a processing unit 30 including a display monitor 39 so as to display ultrasound images.

The at least one probe 20, in some embodiments, is a one-dimensional ultrasound probe 20, which may be steerable or tunable, configured to be placed on the person's head, in one non-limiting example a forehead of the person (and in other embodiments adjacent other portions of the head), and focused on an area in the brain where pulsations of the at least one of brain tissue, brain vessels and ventricles in the head occur. In some embodiments, the area in the brain that the ultrasound or other energy is focused on is at least one of: the third ventricle, lateral ventricles, thalamic striate veins and central cerebral veins of the 3rd ventricular cavity, edges of the 3rd and lateral ventricles, 4th ventricle, choroid plexus veins of ventricles, cavernous and convexital venous sinuses and cortical pulsations. In some embodiments, the area in the brain that the ultrasound energy or other energy is focused on is at least two or at least three of or at least four of or all of the following: the third ventricle, lateral ventricles, thalamic striate veins and central cerebral veins of the 3rd ventricular cavity, edges of the 3rd and lateral ventricles, 4th ventricle, choroid plexus veins of ventricles, cavernous and convexital Venous sinuses and cortical pulsations. For example, the one-dimensional ultrasound probe is in some embodiments configured to operate at a frequency of 0.5-1.5 MHz. The advantage of a one-dimensional ultrasound probe is it penetrates the skull better. In some versions, the ultrasound signals are registered on the sagittal plane 20-50 degrees to the horizontal (axial) plane. The one-dimensional probe 20 is in certain embodiments attached to a region of the head of the person so as to obtain at least one of the following slices: (i) axial, (ii) coronal, (iii) oblique, or so as to be focused in a bi-temporal direction.

In other embodiments of the at least one probe 20, the at least one probe is a two-dimensional ultrasound probe (for example a USB probe) which may be steerable or tunable and configured to be attached to the person's head, in one non-limiting example, at a temporal region of the person's head, and focused on an area in the brain where pulsations of the at least one of brain tissue, brain vessels and ventricles in the head occur. In some embodiments, the area in the brain that the ultrasound energy or other energy is focused on is one of the following: the edges of the third ventricle, the cerebral central vein, and the thalamic striate veins. The advantage of a two-dimensional probe is that the images received are better. In some embodiments, this matters because the technician can discern the reserve space and aim the ultrasound beam more accurately. The two-dimensional ultrasound probe 20 may be configured to operate at a frequency of 1.5-2.5 MHz. The two-dimensional probe 20 is in certain embodiments attached to a region of the head of the person so as to obtain at least one of the following slices: (i) axial, (ii) coronal, (iii) oblique, or so as to be focused in a bi-temporal direction.

In some embodiments a one-dimensional probe is used at one contact point and a two-dimensional probe is used at another contact point simultaneously. While certain areas of the brain have been suggested for the one-dimensional probe and certain areas for the two-dimensional probe these are non-limiting examples and any are of the head allowing access to pulsations of brain tissue and/or ventricles may be utilized. It is noted though that since the forehead is particularly thick, in some embodiments it is useful to make use of a one-dimensional probe when the probe is on the forehead.

Accordingly, apparatus 10 may also include a processing unit 30 including a hardware processor, software and memory, configured to derive from the ultrasound signals an ICP waveform, for example one having a discernable amplitude, whose variations correspond to the pulsations of the pulsating at least one of the brain tissue, the brain vessels and brain ventricles in the head. In some embodiments, the derivation of the ICP waveform is accomplished by a fast Fourier transform performed on the brain pulsations in the chosen area to obtain a distribution of the resonance frequencies in the spectrum. An inverse Fourier transform may then be carried out to reconstruct the noninvasive ICP waveforms of the brain pulsations, for example to reconstruct or render or derive multiaxial volumetric curves of the brain pulsations, for example in real time. In some embodiments, this yields two-dimensional pulsatility which in some embodiments is further converted to three-dimensional or multidimensional pulsatility by including signals from both horizontal and vertical positions held by the at least one probe 20. The term real time as used herein refers to user-perceived real time and in some embodiments means less than 50 milliseconds.

In any version of apparatus 10 herein, apparatus 10 and its components (probe 20, processing unit 30 and pressure mechanism 40) are configured such that in certain embodiments, the application of external pressure (or any portion thereof) is carried out while the at least one probe 20 is being used to generate ultrasound signals and/or while processing unit 30 is being used to derive the ICP waveform from those signals.

Figure 8:
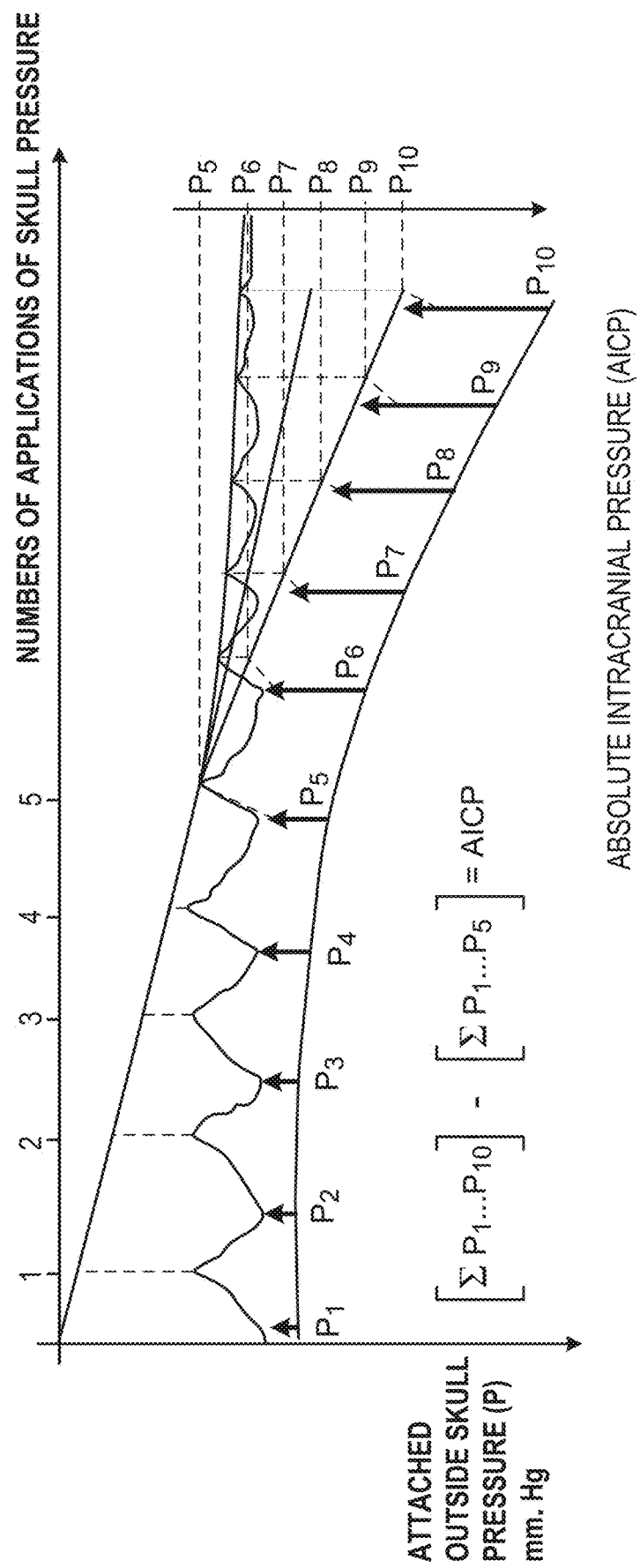
FIG. 8 is a graph showing a decline in amplitude of the ICP waveform, in accordance with an embodiment of the invention.
Figure 9:
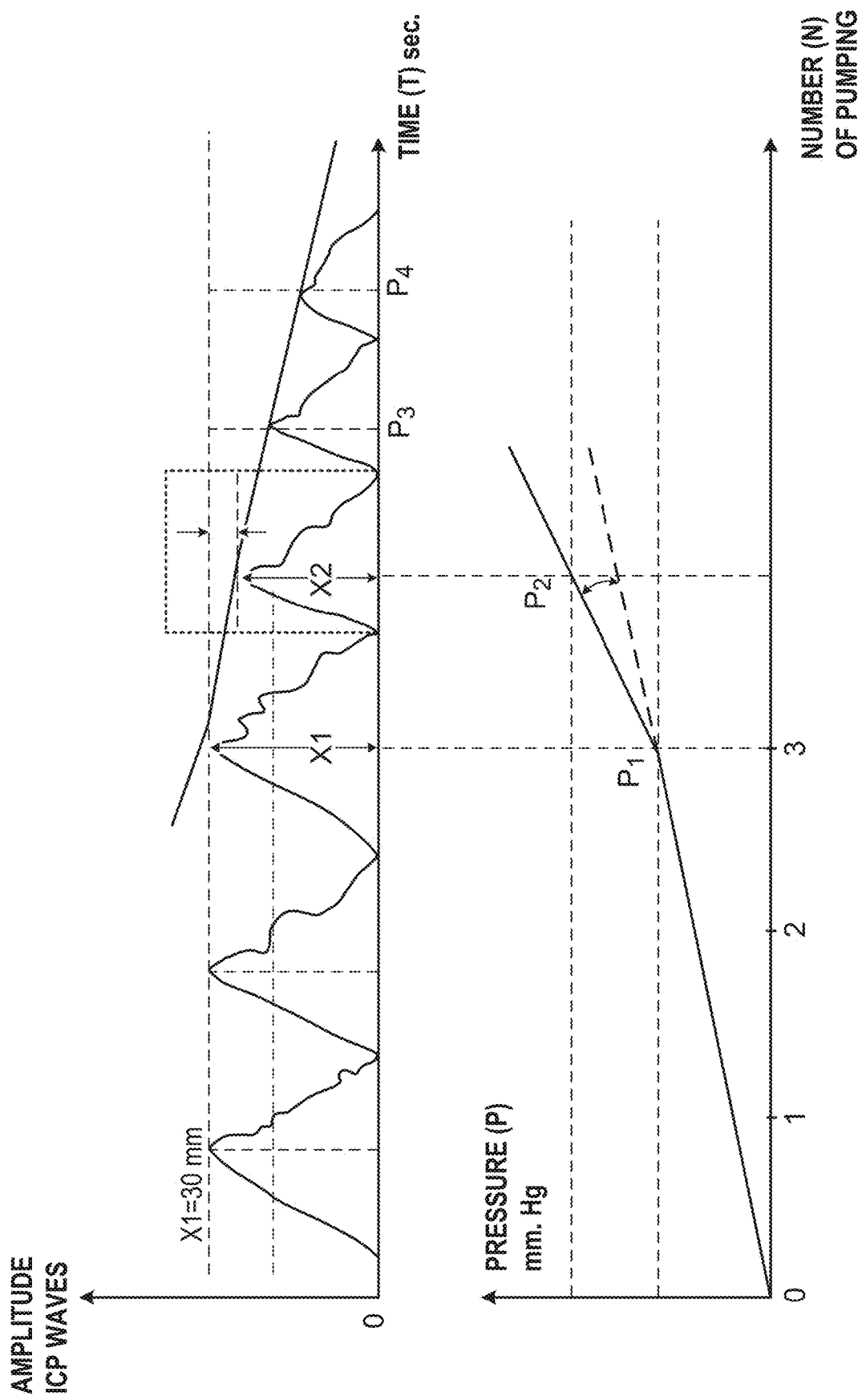
FIG. 9 is graph of amplitude of ICP waveform declining with application of external pressures.

Processing unit 30 is configured to detect a decrease in amplitude of the ICP waveform. As can be appreciated from FIG. 8, this is used in some embodiments to decide which external pressure values to use in the sum of such pressure values to derive the ICP of the person. In FIG. 8, in one embodiment, the sum of $P_5$ through $P_{10}$ or $P_6$ through $P_{10}$ may be used to derive the ICP value of the person. In some embodiments, as can be appreciated from FIG. 7, for example the lower graph, processing unit 30 is also configured to detect a baseline increase and/or a phase shift of the ICP waveform or of its amplitude which confirms the beginning point of the external pressure values in that such beginning point is in some embodiments when there is a decline in amplitude in the waveform that follows a baseline and/or phase shift. In the lower graph of FIG. 7, the decline in amplitude that follows a baseline and/or phase shift occurs after the intermediate period designated in the graph as "ICRS capacity".

Accordingly, in certain embodiments of apparatus 10 (and of method 100), the processing unit 30 is also configured to detect an ICRS intermediate period and when such intermediate period is completed and to identify a decrease in amplitude of the ICP waveform that specifically occurs after the ICRS intermediate period has been completed. As noted, this improves the accuracy of the measurement of the ICP or mean ICP of the person.

The decrease in amplitude that processing unit 30 is configured to detect is a decrease defined to begin at an initial value A1 of the amplitude and which may be as a result of the increase in external pressure. Processing unit 30 is also configured in some embodiments to detect a final value A2. In some embodiments when the amplitude reaches the final value the processing unit 30 is configured to communicate to the pressure mechanism 40 an instruction to halt application of external pressure (or in certain embodiments someone or something other than processing unit 30 such as an operator of apparatus 10 or of pressure mechanism 40 can halt the external pressure when the decrease in amplitude is deemed to reach a final value). Processing unit 30 is configured to determine the ICP of the person from a sum of applied external pressures applied beginning on or after a time of the initial value A1 and ending by a time of the final value A2, wherein one of the following is true:

(i) the final value is a value at which the amplitude remains stable with additional increase(s) in applied external pressure and the processing unit is configured to determine the ICP from the sum of applied external pressures, (ii) the final value A2 is a value to which the amplitude has decreased from the initial value A1 such that at the final value the amplitude is moving towards but has not yet reached the amplitude that remains stable with additional increase(s) in applied external pressure, and the processing unit is configured to determine the ICP or an estimated ICP by extrapolating the sum to a point at which the amplitude remains stable with additional increase in applied external pressure. One example of version "(i)" may be appreciated from FIG. 8 where the initial value may be $P_6$ and the final value is $P_{10}$ in some embodiments. The deformation began between $P_5$ and $P_6$. One example of version "(ii)" from FIG. 8 may be where the initial value may be $P_6$ and the final value is for example $P_7$ and the processing unit 30 extrapolates what $P_8$ through $P_{10}$ would be or is estimated to be using known mathematics, for example based on the rate at which or the percentage by which the amplitude declines between each pressure application.

Typically, the final value (or the extrapolation of the sum of external pressure amounts (or the extrapolation of the external pressure amounts) to the point in time when the amplitude of the waveform has declined to such final value) is very small compared to the initial value and at the final value the amplitude remains stable with an additional increase in applied external pressure after the amplitude has declined considerably. For example, in some embodiments the amplitude would be found to have remained stable with an additional increase in applied external pressure after the amplitude has declined to zero or to a negligible amount or to 1%-5% of the initial value of the amplitude or in other embodiments to 5%-10% (or 10% to 15%) or 15%-20% of the initial value of the amplitude.

In some embodiments in which processing unit 30 is configured to extrapolate the sum of applied external pressures, processing unit 30 in some cases uses a ratio between A1 and a difference between A1 and A2 taking into consideration how many times external pressure was applied from the time of A1 to the time of A2.

There are a number of mathematically sound ways of performing the extrapolation. In one non-limiting example illustrated in FIG. 9, if P1 is the first application of external pressure that occurs after the amplitude of the ICP waveform declines, and P2 is the second such application of external pressure incrementally higher than P1, then if when externally applied pressure goes up from $P_1$ to $P_2$ the amplitude of ICP waveform declines by 25% from $X_1$ (equivalent to A1) to $X_2$, processing unit 30 is configured in some embodiments to extrapolate the sum of applied external pressures by assuming that this sum will be P1+P2+P3+P4+P5 (P5=0) even though P3+P4+P5 never actually occurred. This is because the number of times external pressure will have to be applied before the amplitude of the ICP waveform will remain stable at A2 (namely zero or negligible) will be at most three further increases in applied external pressure and extrapolate the sum of applied external pressures accordingly.

Processing unit 30 in some embodiments is configured to perform image processing algorithms that measure at least three of the following: changes in the baseline, the value of the amplitude, phase shifts, and resonance frequency, of the ICP waveform.

In certain embodiments, the ICP of the person is determined by the processing unit 30 from the sum of applied external pressures (or as the case may be the extrapolated sum of applied external pressures). This is a noninvasive determination representing the person's ICP or absolute ICP or mean ICP (or mean absolute ICP) during the period of time between the initial value to the final value. In some embodiments, this period of time includes at least one systolic cardiac period and at least one diastolic cardiac period of the person's cardiac cycle. In certain non-limiting implementations, this period of time includes at least two or at least three or at least 5 or at least 10 or between 2 and 10 or between 2 and 20 systolic cardiac periods and at least two or at least three or at least 5 or at least 10 or between 2 and 10 or between 2 and 20 diastolic cardiac periods of the person's cardiac cycle.

In certain embodiments, mean ICP of a person is obtained by taking several measurements of ICP noninvasively over a period time (in any of the embodiments described herein) with a hiatus in-between and then averaging these noninvasive ICP measurements together to get "mean ICP" of the person over the total period of time (from the first to the last noninvasive measurement including the hiatuses in-between). In one non-limiting example of this, a noninvasive ICP measurement is taken for anywhere between 2 seconds and 2 minutes, some time is then allowed to pass (whether 15 minutes or 30 minutes or an hour to take several non-limiting examples) and then a further noninvasive ICP measurement is repeated (preferably using the same method used in the first noninvasive measurement). This can go on repeatedly for as long as desired, for example half an hour, an hour, two hours or as long a time as one wants the mean ICP to be based on. Then all these noninvasive ICP measurements are averaged together.

In some embodiments, in order to derive and/or display ICP waveform used to measure (A)ICP, software magnification is used to increase the zoom of a chosen image area, for example of 2-4 $mm^2$ of brain tissue at a depth of 2-17 cm from the surface of the head from the pulsating portion of the image and pulsations of the brain tissue in that area synchronized with the heart rhythm that are caused by the ultrasound energy gradient are observed. A fast Fourier transform in some embodiments is performed on the ultrasound signals from the pulsations of the at least one brain tissue, brain vessel and brain ventricles in the chosen area to obtain a distribution of the resonance frequencies in the spectrum. An inverse Fourier transform may then be carried out to produce curves of the brain pulsations, for example to reconstruct or render or derive multiaxial volumetric curves of the brain pulsations, for example in real time, which are the ICP waveforms.

In some embodiments, artificial intelligence is used to further process the ultrasound signals or to further process the transformed data resulting from application of the Fourier transform and/or fast Fourier transform of such signals. The artificial intelligence may be used in some embodiments to obtain a three dimensional ICP waveform from the signals generated from the two-dimensional ultrasound probe 20.

Once the ICP waveform is displayed on a device such as a digital device which may be a computer screen or a screen of a mobile communication device, e.g. smart phone, a pressure application apparatus 40 (described herein below with respect to FIG. 1 to FIG. 2B) is activated to apply an initial pressure and subsequent greater pressures, for example in uniform stepwise increments, to the outer surface of the head. At some stage, the amplitude of the ICP waveform decreases, which may be as a result of the increase in external pressure. Incremental elevation of the pressure is halted when the signal amplitude remains stable with additional increase in applied pressure or when the amplitude has decreased to a pre-defined ratio from the initial signal amplitude. In some embodiments, the amount of the amplitude decrease induced by the external pressure (and hence the sum of the external pressures needed to reach that declined amount) is proportional to the ICP and is individual to each patient because of its dependence on the skull bone resistance of the patient.

In some embodiments, the invention is carried out using an apparatus that comprises a US probe, a pressure application apparatus, and a processor or computer that comprises a memory, a display device, and software. The processor or computer can be, for example a personal computer, a laptop or tablet computer, a smart phone, or a dedicated device configured to carry out the method.

Apparatus 10 in some embodiments includes a pressure mechanism 40 in communication with the processing unit 30, which may include a pressure applicator 42, configured to apply an external pressure, for example intermittently, to the outer surface of the head by applying an initial external pressure and then incrementally increasing the external pressure applied to the outer surface. In some embodiments, apparatus 10 includes a manometer 44 which may be any device or mechanism for measuring the externally applied pressure.

The external pressure may be applied in uniform stepwise increments. In some embodiments, as shown in FIG. 1, 2a, 2b, 4, 5, the external pressure is applied on each side of the person's head in a bi-temporal direction or in a coronal, axial or oblique direction. In some embodiments of apparatus 10 (or of method 100), "intermittently" means every second or three-quarters of a second or every two seconds or every second and a half. In some versions, the time intervals between applications of pressure is set to correspond to a known or expected time interval between pulsations of the least one of the brain tissue, brain vessels and brain ventricles in the head of the person whose ICP is being measured. Therefore, in some embodiments, the intermittent applications of external pressure is set to correspond to the time interval between two adjacent heart beats of the person, or for example between corresponding portions of the heart beat or heart rhythm of the person (such as between diastolic or systolic portions). The person may have a structure adjacent their head for comfort and to facilitate keeping their head stationary—such structure appears as a rectangle in FIG. 1 and FIG. 2a.

Figure 4:
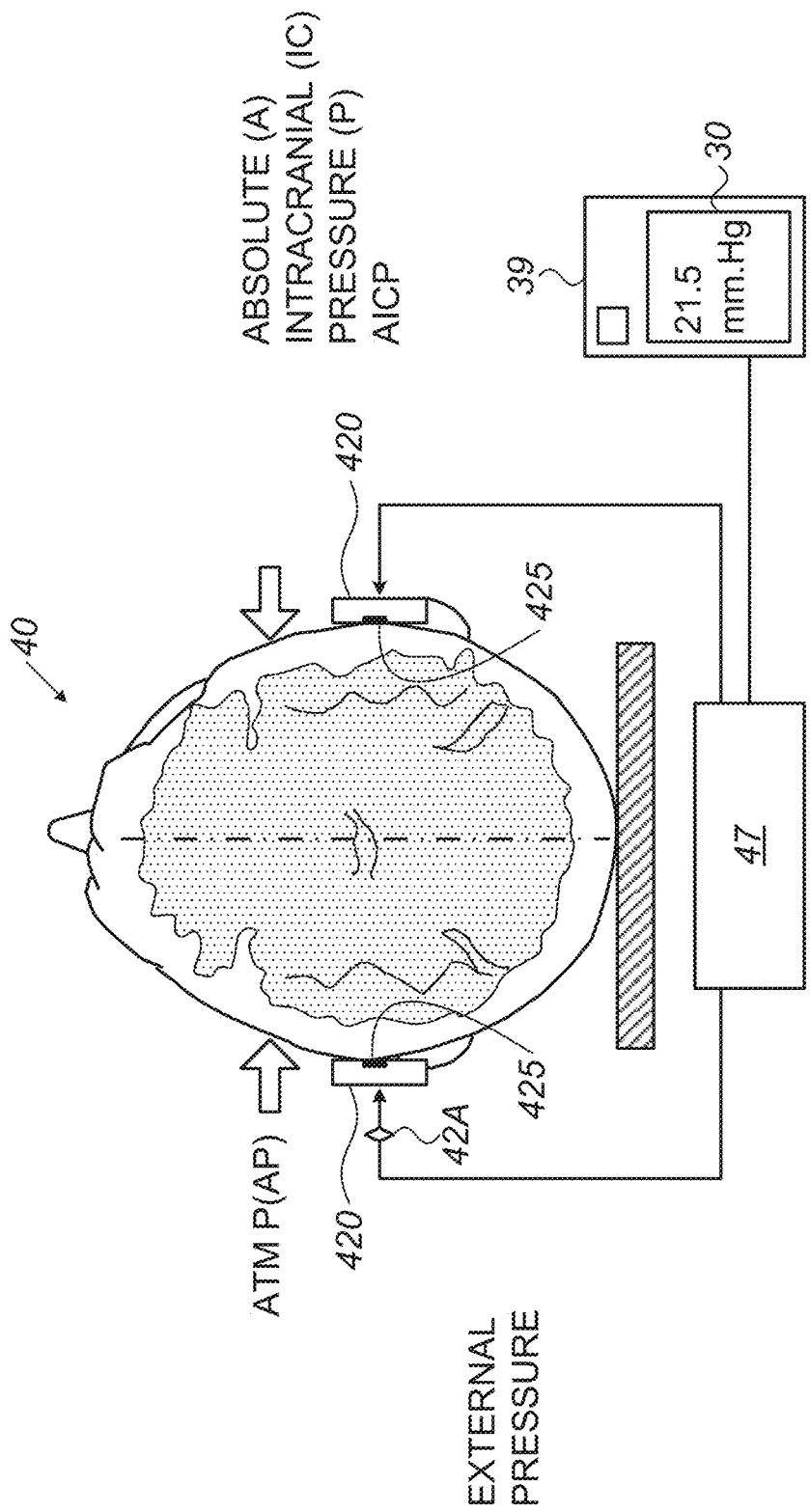
FIG. 4 is a top view schematically showing a mechanism for applying external pressure connected to a motor and processing unit, in accordance with an embodiment of the invention.

In one embodiment, as shown in FIG. 4, a first group of pressure sensors 425 such as tensor sensors is positioned so as to contact the person's skull at one point and a second group of pressure sensors 425 such as tensor sensors is positioned so as to contact a second point of the person's skull, the first and second points being substantially 180 degrees apart. In some embodiments joint 42A is used to ensure contact by sensors to the subject's skull when there are for example three groups of sensors. The sensor may be held by or attached to plates 420.

FIG. 4 shows an example of this where the first and second points are on two different sides of the skull and plates 420 are used to hold the pressure sensors 425. Atmospheric pressure is referred to in FIG. 4 as "ATM P (AP)" but the atmospheric pressure is not used in the determining of mean ICP for the reasons noted and (atmospheric pressure is treated as if it is zero). The invention in certain embodiments is independent of variations in atmospheric pressure.

Figure 5:
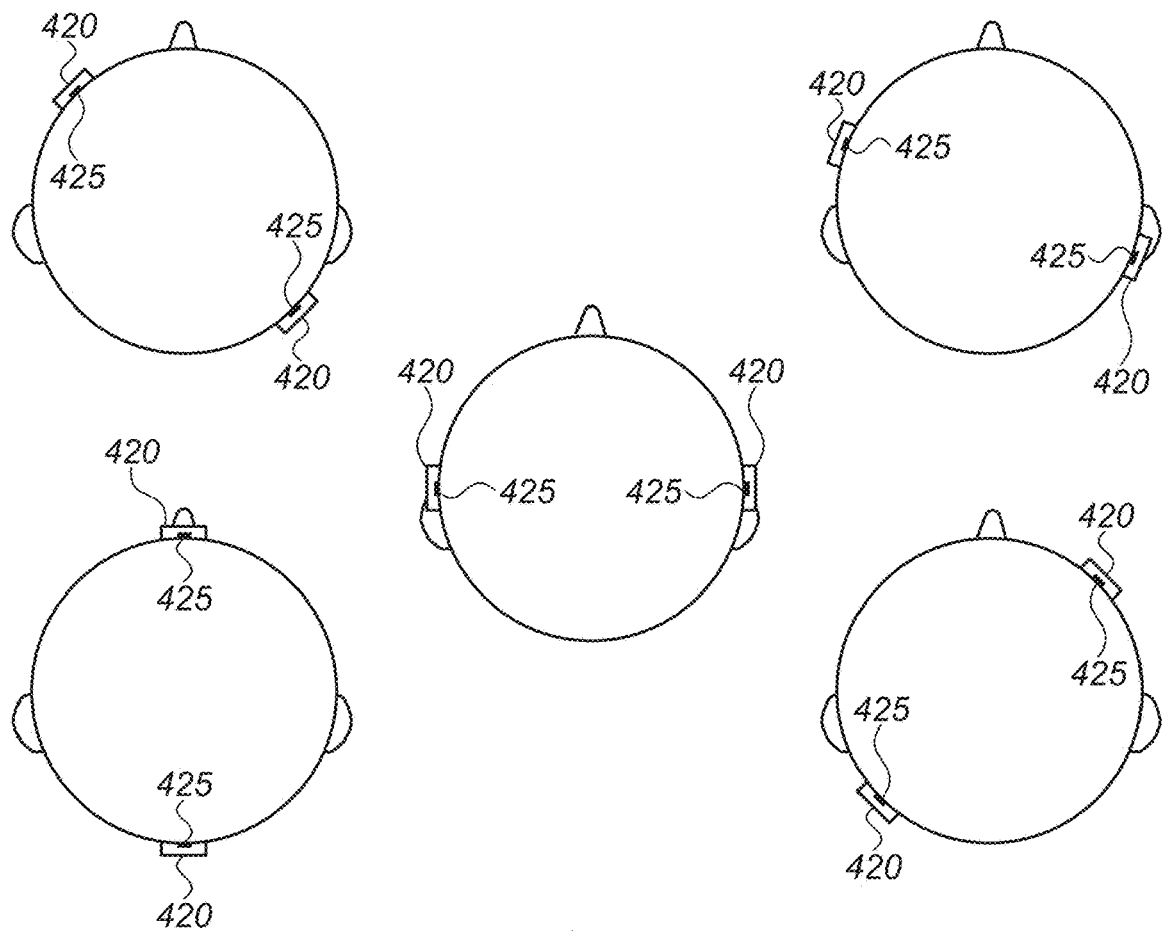
FIG. 5 shows schematic top views of various configurations of contact points for a pressure application mechanism, in accordance with an embodiment of the invention.

FIG. 5 shows another example of this where the two different points are at the front and back of the skull. FIG. 5 shows various non-limiting examples of multiple points of contact for plates 420 that hold or have attached to them pressure sensors 425 including those configured diagonally. Although each example in FIG. 5 shows a single pair of plates 420, in some embodiments there are multiple pairs of plates 420, for example in two, three or more of the configurations shown in FIG. 5 or in FIG. 4.

Figure 6:
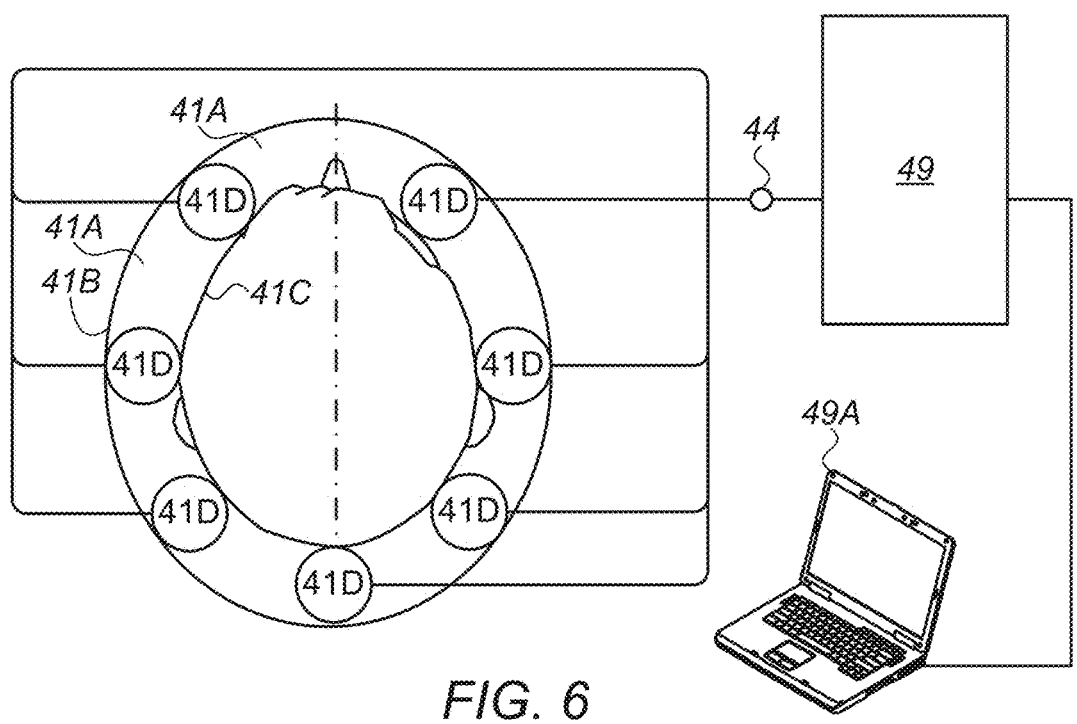
FIG. 6 is a schematic illustration of an alternative pressure application mechanism, in accordance with an embodiment of the invention.
Figure 7:
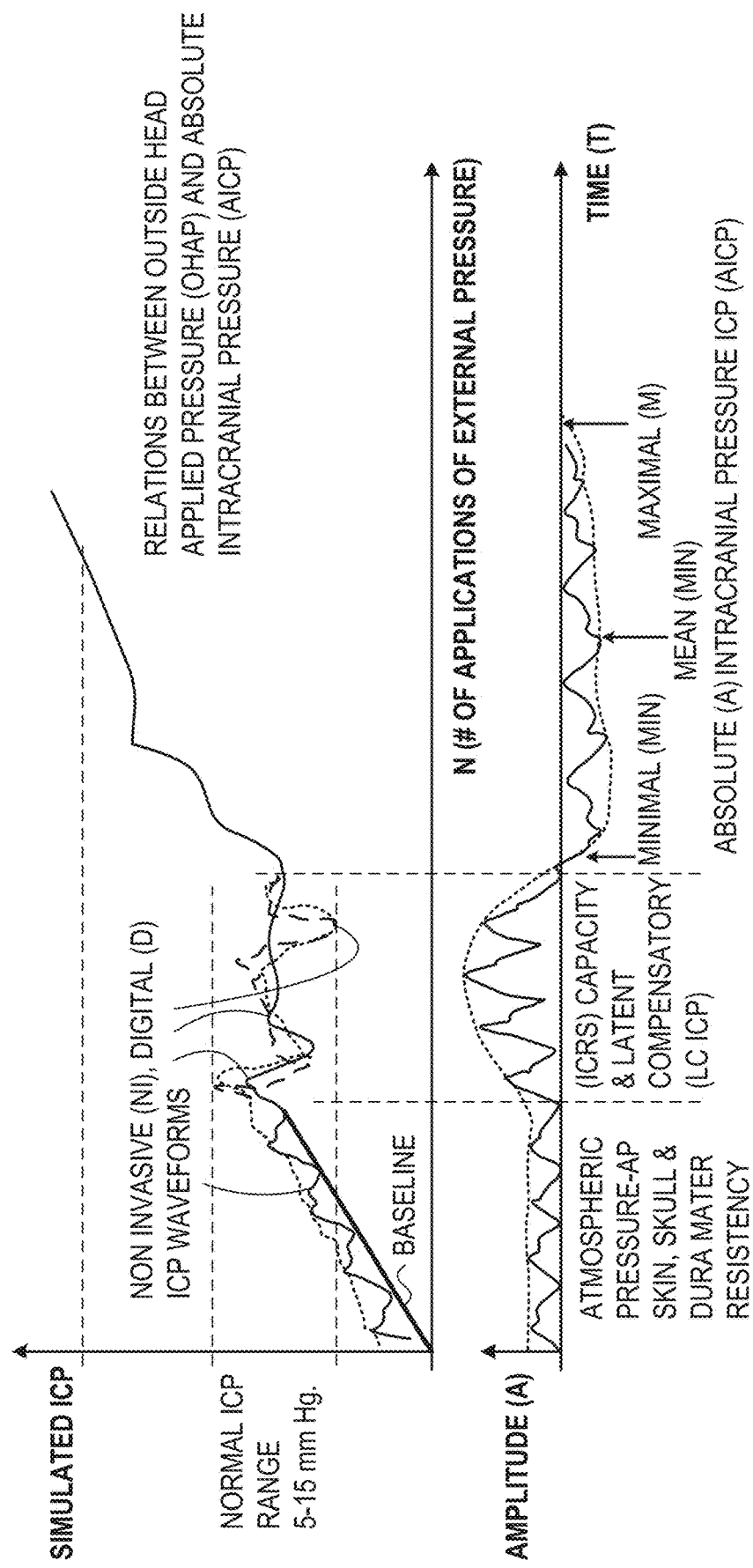
FIG. 7 shows two graphs: the lower graph shows an ICP waveform amplitude varying over time and the upper graph shows a simulation of ICP varying as a result of external pressure applied superimposed with an ICP waveform derived noninvasively, in accordance with an embodiment of the invention.

In another non-limiting embodiment shown in FIG. 6, a helmet 41A is worn by the patient and between the outer wall 41B and inner surfaces/walls 41C of the helmet 41A are balls 41D that contain air or fluid. The balls 41D that represent contact points against the patient's skull. In one implementation, extending from each of the balls 41D on helmet 41A is a tube that connects to a compressor 49. Compressor 49 is configured to fill the balls 41D so as to cause pressure. In the non-limiting version shown in FIG. 6, the tubes converge to a single tube before entering the compressor 49 and a manometer 44 may be positioned there. The compressor 49 may contain a processor 49A or the compressor 49 may be in communication with processing unit 30 such that the compressor 49 is instructed when to apply pressure and through which pair of balls to as to fill in order to apply the external pressure.

Pressure mechanism 40 in some embodiments comprises one of the following: (a) a pressure applicator that includes an inflatable sleeve applied to the person's head or (b) a helmet configured to apply pressure at specific locations on the skull of the person.

In one embodiment shown in FIG. 1, FIG. 2a and FIG. 2b, a pressure application apparatus 41 (see FIG. 2A) comprises two pressure applying components 42, a mechanism 46 for incrementally increasing the pressure, and a manometer 44 is also shown attached to the head of the patient with the pressure applying components 42 on either side of the patient's head such that they can apply pressure to the skull in a bi-temporal direction. The upper graph in FIG. 1 is A mode (one-dimensional) Echo encephalography. The lower graph shows the noninvasive (NI) ICP waves. The left side of the graph shows the (NI) ICP waves before the external pressure is applied to the head and the right side of the graph shows the (NI) ICP waves after pressure is applied. The downward pointing arrow is the place at which the pressure is applied, which causes an elevation in the baseline, a shift in the phase, and a decrease in the amplitude of the (NI) ICP waves. In a second embodiment of the invention, shown schematically in a top view in FIG. 2A and frontal view in FIG. 2B, and in FIG. 3, the measurements are carried out using a steerable two-dimensional (2D) USB Ultrasound probe 20 for 2D sector imaging of a brain (FIG. 3). The scanning is done at a low frequency of 1.5-2.5 MHz, which provides good penetration of the ultrasound beam into the skull cavity. In this embodiment the ultrasound probe 20 is attached to the temporal region of the head and an identical pressure application apparatus 41 is attached to the head in the same manner as in the first embodiment. FIG. 3 shows a 2D ultrasound image 38 taken with the probe 20 described above and the ICP waveform 37 produced by the apparatus from the pulsations from area B. Referring to the ICP waveform in FIG. 3, A1 is the initial amplitude signal when pressure application apparatus 41 begins applying external pressure to the skull at point P. The pressure gradually is increased until it reaches a value P1 at which time the base line rises, the phase of the waveform reverses, and the amplitude of the ICP waveform signal is reduced. A2 is the amplitude of the signal when the external pressure stops being applied, and P2 is the pressure that causes the change in amplitude of the ICP waveform signal from A1 to A2. The (A)ICP is calculated from the measured Pressures (P1, P2) as follows: (A)ICP=(P2−P1) mmHg.

The mechanism for incrementally increasing the pressure 46 can be provided in several different embodiments known in the art. For example, the mechanism 46 can comprise a compressor 49 or a step motor and a piston that causes air or another fluid to travel through conduits to pressure applying components 42 on both sides of the head. In some embodiments there are multiple pistons, as is known in the art of controlled fluid dispensers such as syringes.

Certain embodiments of the apparatus pressure application apparatus 41 include a compressor or a motor and at least one piston movable within a housing, a fluid source of either liquid or gas, for example air, and an applicator 48 that is configured to engage the head of the subject and hold the two pressure applying components 42 in place. Pressure application apparatus 41 may also include a manometer 44 (i.e. any device or mechanism for measuring externally applied pressure) which can be either analog or digital. In certain embodiments, a digital manometer is used so that the instantaneous values of the pressure can be sent to a processor or computer that comprises software algorithms that are configured to use the output signals from the at least one ultrasound probe 43 and manometer 44 to interact with the compressor or motor 47 (FIG. 4) to determine when and what volume of fluid, such as air, should be applied, and when to stop increasing the pressure. The applicator 48 that holds the two pressure applying components 42 in place on the head of the subject can take many forms, for example an elastic band, a Velcro strip, a headphone-like arrangement, or a frame made of plastic or metal. With the exception of the pressure applying components 42, some or all of the other elements of the pressure application apparatus 41 can be either attached to the applicator 48 or can be located remotely to reduce the weight of the applicator 48 and thereby increase the comfort of the patient.

In some embodiments, detection of the compression (decline in amplitude) in the ICP waveform to a predefined decline in amplitude is by either (i) visual detection of the waveform by the user or (ii) automatically performed by the computer apparatus. The computer or processor 30 comprises software algorithms that are configured to process data received from the US probes to produce the ICP waveforms and image processing algorithms that are configured to measure the amplitude of the waveform. The software in the computer or processor of the apparatus is configured to automatically stop increasing the pressure based on either an observation that increasing the pressure does not further decrease the amplitude of the ICP waveform or when the amplitude has become decreased by a predefined percentage of the amplitude before external pressure is applied by pressure application apparatus 1.

In an embodiment of the invention, it is also possible to initially apply a high pressure that will result in an ICP waveform with a low amplitude and incrementally reduce the pressure until the base line becomes lowered, the phase changes, and the amplitude increases. The external pressure in the method as described above is applied in a bi-temporal direction. However, the invention is not limited to the pressure application method as described above. The pressure may be applied in a unilateral direction. Pressure may be applied by other mechanisms, such as (but not limited to) an inflatable sleeve applied on a patient's head, a helmet 41A (FIG. 6) with a pressure application option, or non-contact methods of applying pressure such as by means of a high velocity stream of air, or any other method of controlled pressure application that satisfies the requirements of invention.

Figure 10:
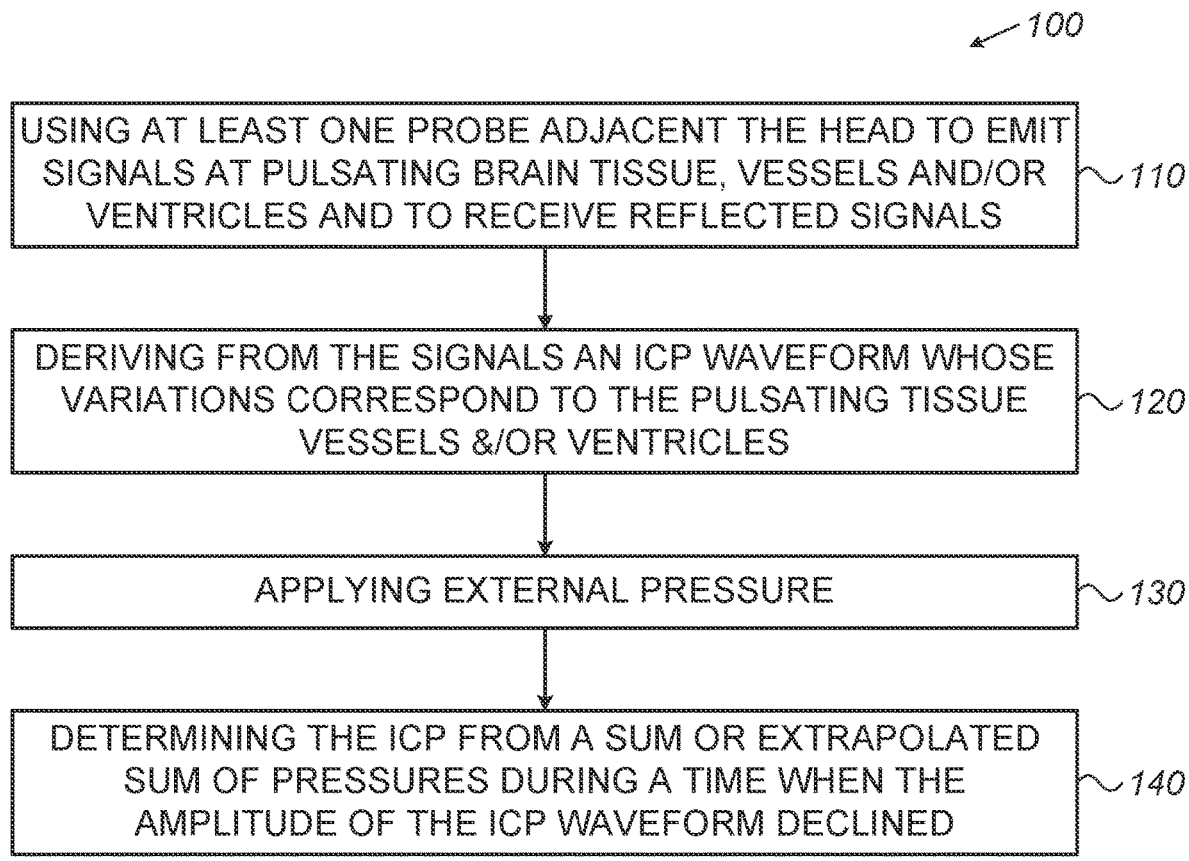
FIG. 10 is a flow chart showing a method, in accordance with an embodiment of the invention.
Figure 11:
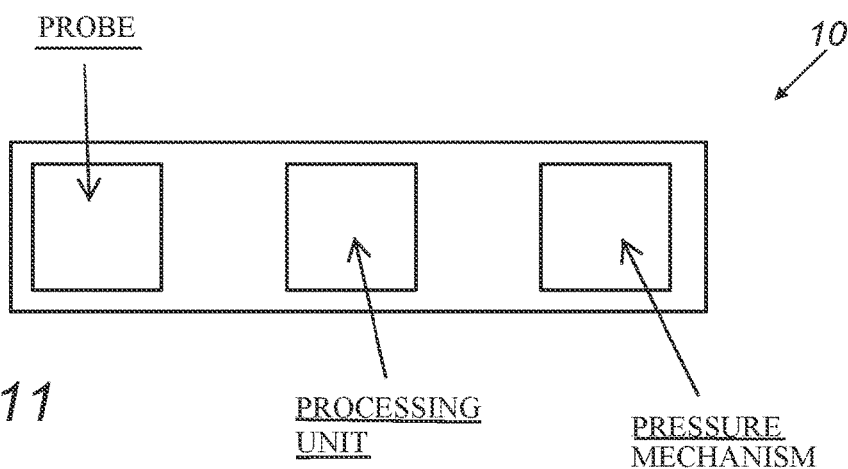
FIG. 11 is a schematic illustration of an apparatus in accordance with an embodiment of the invention.
Figure 12:
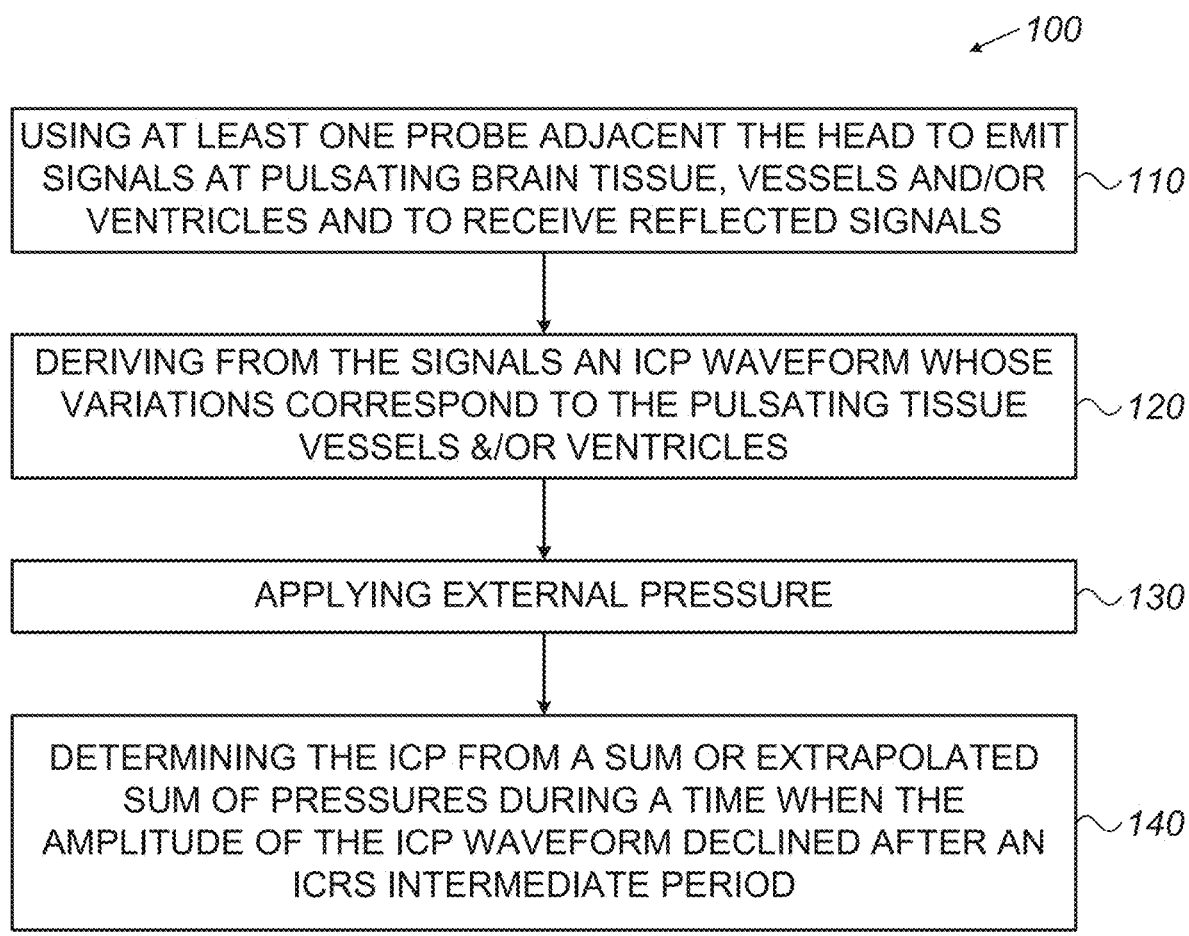
FIG. 12 is a flow chart showing a method, in accordance with an embodiment of the invention.

In one embodiment shown in FIG. 10, the invention is a non-invasive method 100 for measuring (and/or recurrent monitoring of) a mean intracranial pressure (ICP) of a person. Method 100 may comprise a step 110 of using at least one probe (such as probe 20) positioned adjacent an exterior tissue layer of the person's head (such as a soft external tissue layer) to emit energy, for example ultrasound energy, radio waves, near infra red energy, tera hertz frequency energy, at pulsating brain tissue, brain vessels and/or brain ventricles in the head so as to receive reflected signals and/or images associated with the signals. In some embodiments, an ultrasound probe is used to emit ultrasound energy and generate ultrasound energy gradients (for example Cerebral Ergography-CEG) between emitted and reflected ultrasound signals so as to track these pulsations and/or to generate images reflecting the pulsations and/or the signals.

Another step 120 of method 100 may be deriving from the signals, (or from images that are associated with the signals) using a processing unit, for example including a hardware processor, software and memory, an ICP waveform having a discernable amplitude whose variations correspond to the pulsations of the at least one of the brain tissue, brain vessels and brain ventricles in the head.

Method 100 may also comprise a step 130 of applying external pressure intermittently to the outer surface of the head using a pressure mechanism 40 in communication with the processing unit 30, the mechanism 40 including for example a pressure applicator and in some versions also a pressure value measuring component (referred to generally as a manometer). In certain embodiments, the pressure mechanism 40 is designed to apply an initial external pressure and then incrementally increase the external pressure to the outer surface using the applicator. In certain embodiments of method 100, the application of external pressure in step 130 (or any portion thereof) is carried out while step 110 is performed, that is while the at least one probe 20 is being used to generate signals and in some versions and/or while step 120 is performed, that is while the processing unit 30 is being used to derive the ICP waveform from those signals (or images).

In some embodiments, method 100 may also comprise a further step in which, after a decrease in amplitude of the ICP waveform, the decrease beginning at an initial value A1 of the amplitude (which may be as a result of the increase in external pressure), the processing unit 30 instructs the pressure mechanism 40 to halt application of the external pressure when the amplitude reaches a final value A2. In certain embodiments, someone or something other than processing unit 30 halts or sends an instruction to halt the application of external pressure to the person's head.

A further step 140 of method 100 is in some embodiments determining, by the processing unit, the ICP of the person from a sum, or an extrapolated sum, of applied external pressures applied beginning on or after a time of the initial value A1 and ending by a time of the final value A2, wherein one of the following is true: (i) the final value is a value at which the amplitude remains stable with additional increase in applied external pressure and the processing unit is configured to determine the ICP from the sum of applied external pressures, or (ii) the final value A2 is a value to which the amplitude has decreased from the initial value A1 such that at the final value the amplitude is moving towards but has not yet reached the amplitude that remains stable with additional increase in applied external pressure, and the processing unit is configured to determine the ICP or an estimated ICP by extrapolating the sum to a point at which the amplitude remains stable with additional increase in applied external pressure. In certain embodiments of method 100, the processing unit 30 is also configured to detect an ICRS intermediate period and to detect such decrease in amplitude of the ICP waveform that has occurred after the ICRS intermediate period is completed.

One version of method 100 is in a step 110 using at least one probe adjacent the head to emit signals at pulsating brain tissue, vessels and/or ventricles (sometimes referred to as brain tissue and/or brain cavities since vessels are also a kind of tissue) and to receive reflected signals, deriving from the signals an ICP waveform whose variations correspond to the pulsating tissue in a step 120, applying external pressure to the head in a step 130 and in a step 140 determining the ICP from a sum or extrapolated sum of external pressures during a time when the amplitude of the ICP waveform declined.

The method 100 of the invention can be carried out using any version of apparatus 10 described above. In some embodiments, method 100 includes a step of using applying the ultrasound energy using a steerable one-dimensional ultrasound probe (for example an A mode 1-dimensional Echo Encephalography probe) placed on a forehead of the person and focused on an area in the brain where the pulsations occur and the area in the brain is at least one of the following: the third ventricle, lateral ventricles, thalamic striate veins and central cerebral veins of the 3rd ventricular cavity, edges of the 3rd and lateral ventricles, 4th ventricle, choroid plexus veins of ventricles, and cortical pulsations. In some embodiments, the one-dimensional ultrasound probe is operated at a frequency of 0.5-1.5 MHz. In some versions, ultrasound signals are registered on the sagittal plane 20-50 degrees to the horizontal (axial) plane. The measurements may instead (or in addition to simultaneously) be carried out using a steerable two-dimensional (2D) ultrasound probe attached to a temporal region of the head and focused on an area in the brain where pulsations of the brain tissues occur. The two-dimensional US probe may be operated at a frequency of 1.5-2.5 MHz.

The area in the brain may be one of the following: the edges of the third ventricle, the cerebral central vein, and the thalamic striate veins (or may be at least one of the following: the third ventricle, lateral ventricles, thalamic striate veins and central cerebral veins of the 3rd ventricular cavity, edges of the 3rd and lateral ventricles, 4th ventricle, choroid plexus veins of ventricles, and cortical pulsations).

In certain embodiments of method 100, the external pressure is applied in uniform stepwise increments. The external pressure may be applied on each side of the person's head in a bi-temporal direction.

In some versions of method 100, processing unit may be configured to extrapolate the sum using a ratio between A1 and a difference between A1 and A2 taking into consideration how many times external pressure was applied from the time of A1 to the time of A2.

In some versions of method 100, deriving the ICP waveform from the ultrasound signals is accomplished by a fast Fourier transform performed on the brain pulsations in the area of the brain where pulsations of the brain tissue occur to obtain a distribution of the resonance frequencies in the spectrum and an inverse Fourier transform is performed to reconstruct curves of the brain pulsations, for example to reconstruct or render or derive multiaxial volumetric curves of the brain pulsations, for example digital real time patterns of the brain pulsations.

In one non-limiting embodiment of method 100, the probe 20 is a steerable one-dimensional (1D). FIG. 1 is a schematic view looking at the top of the patient's head. In this method, a one-dimensional US probe 3 with frequency of 0.5-1.5 MHz is placed on the forehead of the patient and focused on the area in the brain to be analyzed, i.e. an area where pulsations of the brain tissues are observed, e. g. the third ventricle 7 as shown in FIG. 1 or the cerebral central vein, or the thalamic striate veins. The signal is registered on the sagittal plane 20-50 degrees to the horizontal (axial) plane.

In some embodiments, the derivation of the ICP waveform is accomplished by a fast Fourier transform performed on the brain pulsations in the chosen area to obtain a distribution of the resonance frequencies in the spectrum. An inverse Fourier transform may then be carried out to produce curves of the brain pulsations, for example in real time.

A still further embodiment of the invention is an apparatus 10 for non-invasive measurement (and/or for recurrent monitoring) of mean intracranial pressure (ICP) of a person, comprising at least one probe 20 (for example at least one ultrasound probe 20) configured to be positioned adjacent an exterior tissue layer of the person's head and to emit energy at pulsating one or more of brain tissue, brain vessels and brain ventricles of the person's head and to receive reflected signals; a processing unit 30 configured to derive from the signals or from images associated with these signals an ICP waveform (for example having a discernable amplitude); a pressure mechanism 40 in communication with the processing unit 30 and configured to apply an external pressure intermittently to the outer surface of the head. In some embodiments, the processing unit 30 is configured to detect a decrease in amplitude of the ICP waveform, the decrease beginning at an initial value A1 of the amplitude (for example as a result of the increase in external pressure) and to detect a final value A2. In some embodiments, the processing unit 30 is configured to communicate to the pressure mechanism 40 an instruction to halt external pressure when the amplitude reaches the final value or such halt may occur through intervention of an operator or another component. In some embodiments, the processing unit 30 is configured to determine the ICP of the person either from a sum of applied external pressures applied beginning on or after a time of the initial value A1 and ending by a time of the final value A2, or from an extrapolated sum of applied external pressures. In certain embodiments, the processing unit 30 is also configured to detect an ICRS intermediate period and to detect such decrease in amplitude of the ICP waveform that has occurred after the ICRS intermediate period is completed.

A yet still further embodiment of the invention is an apparatus for non-invasive measurement of mean intracranial pressure (ICP) of a person, comprising at least one probe configured to be positioned on an outer surface of the person's head and to emit energy at pulsating tissue (in this embodiment broadly speaking "brain tissue" includes brain vessels since vessels are a kind of tissue, in contrast to cavities) or cavities in the brain or head (for example at pulsating one or more of brain tissue, brain vessels and brain ventricles of the person's head) and to receive reflected signals; a processing unit configured to derive from the signals or from images associated with the signals an ICP waveform; a pressure mechanism in communication with the processing unit and configured to apply an external pressure to the outer surface of the head (and in some embodiments to measure the applied external pressure), wherein the processing unit is configured to detect a decrease in an amplitude of the ICP waveform, the decrease having a starting point and an endpoint, and to determine an ICP such as a mean ICP of the person either from a sum of applied external pressures applied during the decrease or from an extrapolated sum of applied external pressures applied during the decrease.

Any implementation of the at least one probe 20, processing unit 30 or pressure mechanism 40 described herein may be used for apparatus 10.

Furthermore, method 100 may be implemented using any version of the apparatus 10 mentioned in this patent application.

While the invention has been described with respect to a limited number of embodiments, it will be appreciated that many variations, modifications and other applications of the invention may be made. Therefore, the claimed invention as recited in the claims that follow is not limited to the embodiments described herein.

What is claimed is:

1. A non-invasive method for measuring an intracranial pressure (ICP) of a person, comprising:
    using at least one probe configured to be positioned so as to emit energy at pulsating tissue or cavities in the brain of the person and to receive reflected signals;
    deriving from the signals or from images associated with the signals, using a processor, an ICP waveform;
    applying an external pressure, and then incrementally increasing the external pressure, to the person's skull using a pressure mechanism in communication with the processor, the pressure mechanism including a pressure applying component having at least one surface and a manometer and configured to apply the external pressures including the incrementally increased external pressures, to the person's skull when the at least one surface contacts the person's skull;
    detecting, using the processor, a decrease in amplitude of the ICP waveform, the decrease beginning at an initial value A1 of the amplitude, and a final value A2,
    detecting, using the processor, an intracranial reserve space (ICRS) intermediate period and detecting such decrease in amplitude of the ICP waveform that occurs after the ICRS intermediate period is completed; and
    determining, using the processor, the ICP of the person as a function of values of the applied external pressures applied beginning on or after a time of the initial value A1 and ending by a time of the final value A2 or earlier,
    wherein the values of the applied external pressures include the values of the applied incrementally increased external pressures.

2. The method of claim 1, wherein one of the following is true:
    (i) the final value A2 is a value at which the amplitude reaches a predefined absolute or relative amount with additional increase in applied external pressure and the processor is configured to determine the ICP from a sum of the values of the applied external pressures,
    (ii) the final value A2 is a value to which the amplitude has decreased from the initial value A1 such that at the final value the amplitude is moving towards but has not yet reached the amplitude that is the predefined absolute or relative amount with additional increase in applied external pressure, and the processor is configured to determine the ICP or an estimated ICP by extrapolating a sum of the values of the applied external pressures to a point at which the amplitude reaches the predefined absolute or relative amount with additional increase in applied external pressure.

3. The method of claim 1, further comprising using the processor to perform image processing algorithms that measure at least one of the following: changes in a baseline, the value of the amplitude, phase shifts, and resonance frequency, of the ICP waveform.

4. The method of claim 1, further comprising using the processor to perform image processing algorithms that measure at least two of the following: changes in a baseline, the value of the amplitude, phase shifts, and resonance frequency, of the ICP waveform.

5. The method of claim 1, further comprising using the processor to perform image processing algorithms that measure at least three of the following: changes in a baseline, the value of the amplitude, phase shifts, and resonance frequency, of the ICP waveform.

6. The method of claim 1, further comprising applying the energy using a steerable one-dimensional ultrasound probe placed on a forehead of the person and focused on an area in the brain where pulsations of the pulsating tissue or cavities occur.

7. The method of claim 6, wherein the one-dimensional ultrasound probe is configured to operate at a frequency of 0.5-1.5 MHz.

8. The method of claim 6, wherein the area in the brain is at least one of: the third ventricle, lateral ventricles, thalamic striate veins and central cerebral veins of the 3rd ventricular cavity, edges of the 3rd and lateral ventricles, 4th ventricle, choroid plexus veins of ventricles, and cortical pulsations.

9. The method of claim 6, wherein the signals are registered on the sagittal plane 20-50 degrees to the horizontal (axial) plane.

10. The method of claim 1, further comprising applying the energy using a steerable two-dimensional USB ultrasound probe configured to be attached to a temporal region of a head of the person or attached so as to obtain at least one of (i) an axial slice, (ii) a coronal slice, (iii) an oblique slice, the two-dimensional probe focused on an area in the brain where pulsations of the one or more of brain tissue, brain vessels and brain ventricles occur.

11. The method of claim 10, wherein the two-dimensional ultrasound probe is configured to operate at a frequency of 1.5-2.5 MHz.

12. The method of claim 10, wherein the area in the brain is one of the following: the edges of the third ventricle, the cerebral central vein, and the thalamic striate veins.

13. The method of claim 1, wherein the external pressure is applied on each side of the person's head in a bi-temporal direction or in a coronal, axial or oblique direction.

14. The method of claim 1, further comprising using the processor to derive the ICP waveform from the signals using a fast Fourier transform performed on the signals derived from the pulsating tissue or cavities in the brain to obtain a distribution of resonance frequencies in a spectrum.

15. The method of claim 1, further comprising using the processor to perform an inverse Fourier transform to produce noninvasive ICP waveforms of the pulsating tissue or cavities.

16. The method of claim 1, further comprising positioning the at least one probe adjacent the person's head, wherein the probe is configured to emit ultrasound energy and wherein the ICP waveform has variations that correspond to the pulsating tissue or cavities in the brain.

17. An apparatus for non-invasive measurement of an intracranial pressure (ICP) of a person, comprising:
at least one probe configured to be positioned so as to emit energy at pulsating tissue or cavities in the brain and to receive reflected signals;
a processor configured to derive from the signals or from images associated with the signals an ICP waveform; and
a pressure mechanism, including a pressure applying component having at least one surface and a manometer, in communication with the processor configured to apply an external pressure to the person's skull using the at least one surface of the pressure mechanism,
wherein the processor is configured to detect a decrease in amplitude of the ICP waveform, the decrease beginning at an initial value A1 of the amplitude, and to detect a final value A2,
wherein the processor is configured to detect an intracranial reserve space (ICRS) intermediate period and to detect such decrease in amplitude of the ICP waveform that occurs after the ICRS intermediate period,
wherein the processor is configured to determine the ICP of the person as a function of values of the applied external pressure applied beginning on or after a time of the initial value A1 and ending by a time of the final value A2 or earlier.

18. The apparatus of claim 17, wherein the pressure mechanism is configured to incrementally increase the external pressure before the processor detects the final value of the amplitude.

19. The apparatus of claim 17, wherein the at least one probe is a steerable one-dimensional ultrasound probe configured to be placed on a forehead of the person and focused on an area in the brain where pulsations of the brain tissues occur.

20. The apparatus of claim 19, wherein the one-dimensional ultrasound probe is configured to operate at a frequency of 0.5-1.5 MHz.

21. The apparatus of claim 19, wherein the signals are registered on the sagittal plane 20-50 degrees to the horizontal (axial) plane.

22. The apparatus of claim 17, wherein the at least one probe is a steerable two-dimensional USB ultrasound probe configured to be attached to a temporal region of the head or attached so as to obtain at least one of (i) an axial slice, (ii) a coronal slice, (iii) an oblique slice, the two-dimensional probe focused on an area in the brain where pulsations of the one or more of brain tissue, brain vessels and brain ventricles occur.

23. The apparatus of claim 22, wherein the two-dimensional ultrasound probe is configured to operate at a frequency of 1.5-2.5 MHz.

24. The apparatus of claim 22, wherein the area in the brain is one of the following: the edges of the third ventricle, the cerebral central vein, and the thalamic striate veins.

* * * * *